United States Patent [19]
Becker et al.

[11] Patent Number: 5,858,192
[45] Date of Patent: Jan. 12, 1999

[54] METHOD AND APPARATUS FOR MANIPULATION USING SPIRAL ELECTRODES

[75] Inventors: Frederick F. Becker, Houston; Peter R. C. Gascoyne, Bellaire; Ying Huang; Xiao-Bo Wang, both of Houston, all of Tex.

[73] Assignee: Board of Regents, The University of Texas System, Austin, Tex.

[21] Appl. No.: 733,508

[22] Filed: Oct. 18, 1996

[51] Int. Cl.$^6$ .......................... G01N 27/26; C25B 11/02
[52] U.S. Cl. .................. 204/547; 204/280; 204/643; 436/149; 436/806
[58] Field of Search .................. 204/547, 670; 7/400, 280, 643; 436/149, 806

[56] References Cited

U.S. PATENT DOCUMENTS

| | | | |
|---|---|---|---|
| 4,001,102 | 1/1977 | Batha et al. | 204/186 |
| 4,326,934 | 4/1982 | Pohl | 204/180 |
| 4,440,638 | 4/1984 | Judy et al. | 210/198.2 |
| 4,476,004 | 10/1984 | Pohl | 435/285.2 |
| 5,344,535 | 9/1994 | Betts et al. | 204/183.1 |
| 5,454,472 | 10/1995 | Benecke et al. | 209/127.1 |
| 5,489,506 | 2/1996 | Crane | 435/2 |
| 5,569,367 | 10/1996 | Betts et al. | 204/547 |

FOREIGN PATENT DOCUMENTS

| | | |
|---|---|---|
| 1-196566 | 8/1989 | Japan . |
| 5-126796 | 5/1993 | Japan . |
| 6-18523 | 1/1994 | Japan . |
| 474723 A | 6/1975 | U.S.S.R. . |
| 2266153 | 10/1993 | United Kingdom . |
| WO 91/11262 | 8/1991 | WIPO . |
| WO 93/20927 | 10/1993 | WIPO . |
| 94/16821 | 8/1994 | WIPO . |
| WO 94/16821 | 8/1994 | WIPO . |
| WO 94/22583 | 10/1994 | WIPO . |
| 96/31282 | 10/1996 | WIPO . |
| WO 96/31282 | 10/1996 | WIPO . |

OTHER PUBLICATIONS

Moesner et al. ("New considerations for traveling wave paricle handling", Conf. Rec. IEEE Ind. Appl. Conf., IAS Annu. Meet., 31st (1996), vol. 4, 1986–1993), Oct. 10, 1996.
Wang et al. ("Non–uniform spatial distributions of both the magnitude an phase of AC eelctric fields determine dielecric forces", Biochimica et Biophysic Acta 1243 (1995), pp. 185–194) month unavailabe 1995.
Becker et al. ("Separation of human breast cancer cells from blood by differential dielectric affinity", Proc. Natl. Acad. Sci. U.S.A. (1995), 92(3), 860–4) month unavailable 1995.
Davis et al., "Feasibility Study of Dielectrical Field–Flow Fractionation," Separtion Science and Technology, 21(9):969–989, 1986. month unavailable.
International Search Report dated Jul. 9, 1997 (UTFC:524P).
Arnold and Zimmerman, "Rotation of an Isolated Cell in a Rotating Electric Field," *Naturwissenschaften,* 69:297–298, 1982. month unavailable.
Becker et al., "Separation of human breast cancer from flood by differential dielectric affinity," *Proc. Natl. Acad. Sci. USA,* 92:860–864, Jan., 1995.
Becker et al., "The removal of human leukaemia cells from blood using interdigitated microelectrodes," *J. Phys. D. Appl. Phys.,* 27:2659–2662, 1994. month unavailable.

(List continued on next page.)

*Primary Examiner*—Robert Warden
*Assistant Examiner*—Alex Noguerda
*Attorney, Agent, or Firm*—Arnold, White & Durkee

[57] ABSTRACT

The present disclosure is directed to a novel apparatus and novel methods for the separation, characterization, and manipulation of matter. In particular, the invention combines the use of frequency-dependent dielectric and conductive properties of particulate matter and solubilized matter with the properties of a suspending medium to discriminate and separate such matter. The apparatus includes a chamber having at least one spiral electrode element. Matter is separated in the chamber by a dielectrophoretic (DEP) force caused by the energized electrode or electrodes.

48 Claims, 19 Drawing Sheets

OTHER PUBLICATIONS

Fuhr, *Über die rotation dielektrischer körper in rotierenden feldern*, Ph.D. Dissertation, Humboldt–Universität, Berlin, Chap. 3, pp. 24–53, 1985. month unavailable.

Gascoyne et al., "Dielectrophoretic Separation of Cancer Cells from Blood," presented at the Institute for Electrical Engineers Industrial Application Society meeting, Orlando, Florida, Oct., 1995.

Gascoyne et al., "Dielectrophoretic separation of mammalian cells studied by computerized image analysis," *Meas. Sci. Technol.*, 3:439–445, 1992. month unavailable.

Gascoyne et al., "Manipulation of erythroleukemia cells using travelling electric fields," *Proc.. 16th IEEE–Eng. Med. Biol. Soc.*, 772–773, 1994.

Gascoyne et al., "Numerical analysis of the influence of experimental conditions on the accuracy of dielectric parameters derived from electrorotation measurements," *Bioelectrochemistry and Bioenergetics*, 36:115–125, 1995. month unavailable.

Gascoyne et al., "Cell Separation by Conventional Dielectrophoresis Combined with Field–Flow–Fractionation," *Abstract*, 40th Annual Meeting, Baltimore, Maryland, pp. A333, 17–21 Feb., 1996.

Giddings, "Field–Flow Fractionation: Analysis of Macromolecular, Colloidal, and Particulate Materials," *Science*, 260:1456–1465, Jun., 1993.

Hagedorn et al., "Travelling–wave dielectrophoresis of microparticles," *Electrophoresis*, 13:49–54, 1992. month unavailable.

Hölzel and Lamprecht, "Dielectric properties of yeast cells as determined by electrorotation," *Biochim. Biophys. Acta*, 1104:195–200, 1992. month unavailable.

Huang et al., "Differences in the AC electrodynamics of viable and non–viable yeast cells determined through combined dielectrophoresis and electrorotation studies," *Phys. Med. Biol.*, 37:1499–1517, 1992. month unavailable.

Huang et al., "Application of AC Electrokinetics for Cell Characterization and Manipulation," *Abstract*, 40th Annual Meeting, Baltimore, Maryland, pp. A334, 17–21 Feb., 1996.

Huang et al., "Electrorotational studies of the cytoplasmic dielectric properties of Friend murine erythroleukaemia cells," *Phys. Med. Biol.*, 40:1789–1806, 1995. month unavailable.

Huang et al., "Electrokinetic behaviour of colloidal particles in travelling electric fields: studies using yeast cells," *J. Phys. D. Appl. Phys.*, 26:1528–1535, 1993. month unavailable.

Markx et al., "Dielectrophoretic characterization and separation of micro–organisms," *Microbiol.*, 140:585–591, 1994. month unavailable.

Markx and Pethig, "Dielectrophoretic Separation of Cells: Continuous Separation," *Biotechnology and Bioengineering*, 45:337–343, 1995. month unavailable.

Wang et al., "A unified therory of dielectrophoresis and travelling wave dielectrophoresis," *J. Phys. D. Appl. Phys.*, 27:1571–1574, 1994. month unavailable.

Wang et al., "Dielectrophoretic Manipulation of Cells Using Spiral Electrode Arrays," *Abstract*, 440th Annual Meeting, Baltimore, Maryland, p. A333, 17–21 Feb., 1996.

Wang et al., "Dielectrophoretic Manipulation of Particles," presented at The Institute for Electrical Engineers Industrial Application Society meeting, Orlando, Florida, Oct., 1995.

Wang et al., "Non–uniform spatial distributions of both the magnitude and phase of AC electric fields determine dielectrophoretic forces," *Biochimica et. Biophysica Acta*, 1243:185–194, 1995. month unavailable.

Wang et al., "Changes in Friend murine erythroleukaemia cell membranes during induced differentiation determined by electrorotaion," *Biochimica et Biopysica Acta*, 1193:330–334, 1994 month unavailable.

Washizu et al., "Molecular Dielectrophoresis of Biopolymers," *IEEE Trans on Industry App*, 30(4):835–843, Aug. 1994.

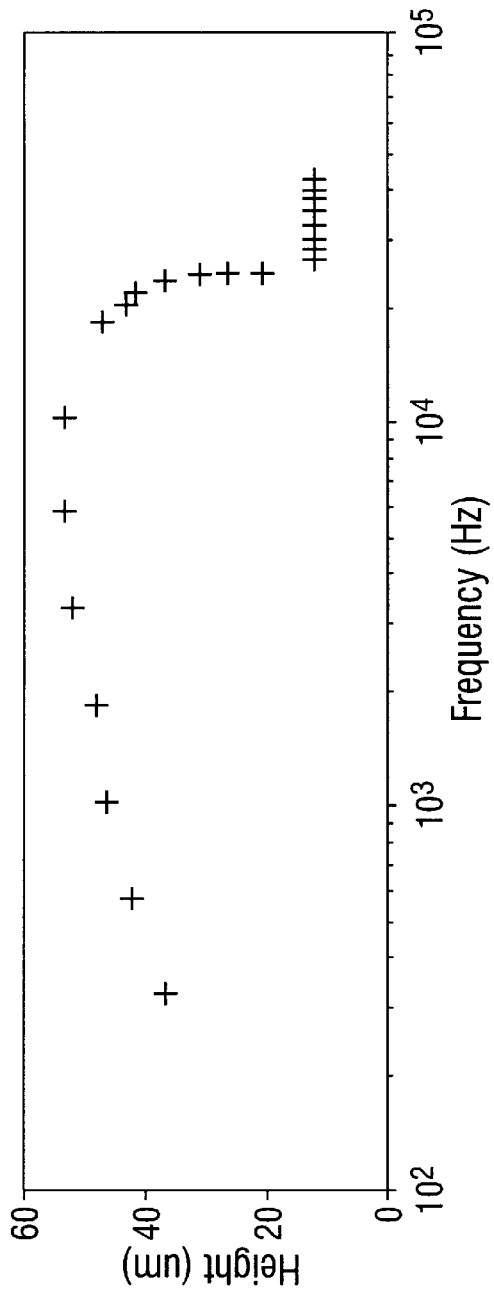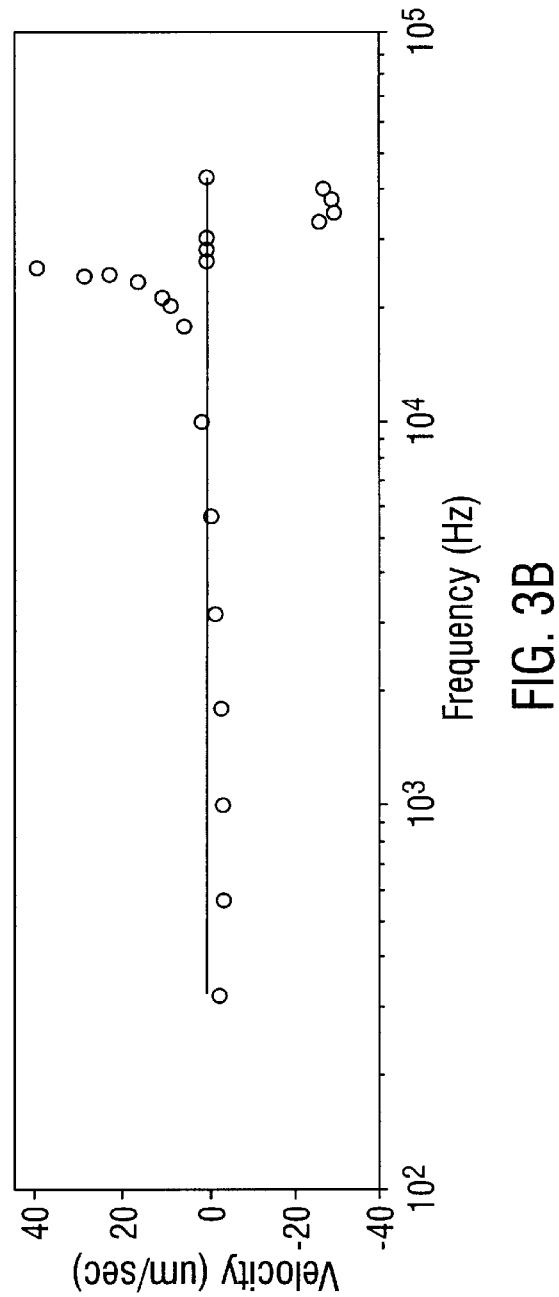

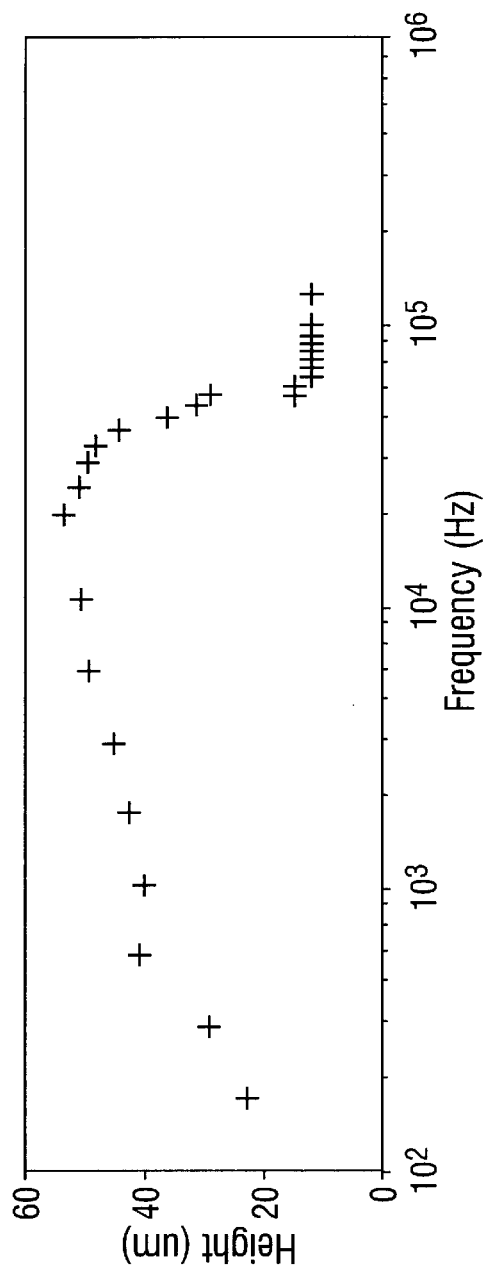
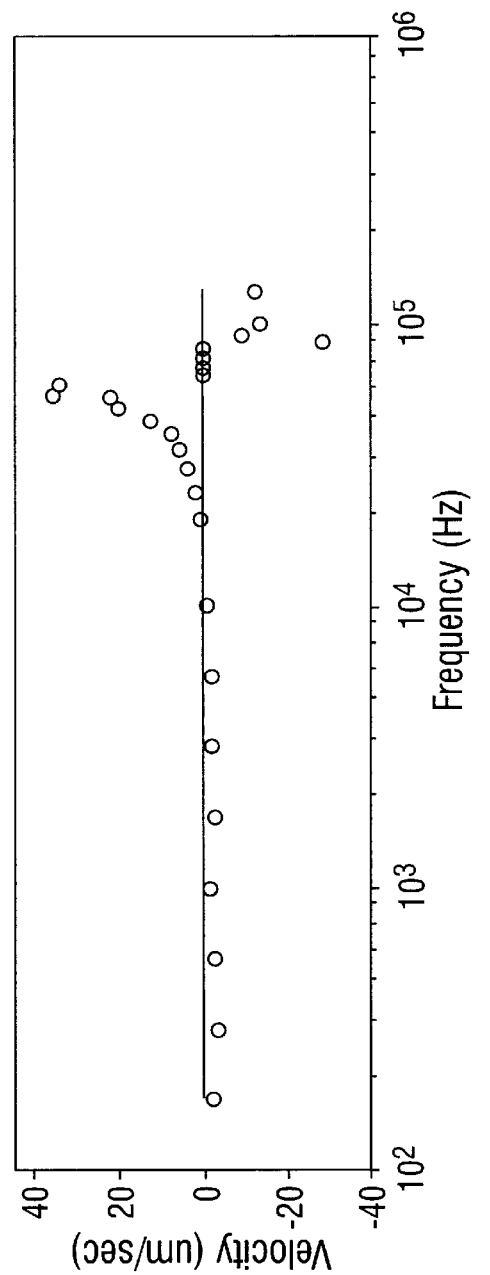
FIG. 3C
FIG. 3D

METHOD AND APPARATUS FOR MANIPULATION USING SPIRAL ELECTRODES

BACKGROUND OF THE INVENTION

1. Field of the Invention

The present invention relates generally to the fields of molecular separation and particle discrimination. More particularly, it concerns the manipulation of particulate matter utilizing a combination of electrical, hydrodynamic or gravitational forces, which may be useful in diagnostic procedures.

2. Description of the Related Art

The ability to identify, characterize and purify cell subpopulations is fundamental to numerous biological and medical applications, often forming the starting point for research protocols and the basis for current and emerging clinical protocols. Cell separation has numerous applications in medicine, biotechnology, and research in environmental settings. For example, cell separation can make possible life-saving procedures such as autologous bone marrow transplantation for the remediation of advanced cancers where the removal of cancer-causing metastatic cells from a patient's marrow is necessitated (Fischer, 1993). In other applications, such as the study of signaling between blood cells (Stout, 1993), (Cantrell et al., 1992), highly purified cell subpopulations permit studies that would otherwise be impossible. Current approaches to cell sorting most frequently exploit differences in cell density (Boyum, 1974), specific immunologic targets (Smeland et al., 1992), or receptor-ligand interactions (Chess and Schlossman, 1976) to isolate particular cells.

These techniques are often inadequate and sorting devices capable of identifying and selectively manipulating cells through novel physical properties are therefore desirable. The application of the principles of AC electrokinetics has been used for the dielectric characterization of mammalian cells through the method of electrorotation (ROT) (Arnold and Zimmermann, 1982; Fuhr, 1985; Hölzel and Lamprecht, 1992; Wang et al., 1994) and for cell discrimination and sorting (Hagedorn et al., 1992; Huang et al., 1993; Gascoyne et al., 1992; Gascoyne et al., 1994; Huang et al., 1992). In these techniques, cells become electrically polarized when they are subjected to an AC electric field. If that field is inhomogeneous, then the cells experience a lateral dielectrophoretic (DEP) force, the frequency response of which is a function of their intrinsic electrical properties (Gascoyne et al., 1992). In turn, these properties depend strongly on cell composition and organization, features that reflect cell morphology and phenotype. Cells differing in their electrical polarizabilities can thus experience differential forces in the inhomogeneous electric field (Becker et al., 1994; Becker et al., 1995). Analysis of the dielectrophoretic motion of mammalian cells as a function of applied frequency permits cell membrane biophysical parameters, such as capacitance and surface conductance, to be probed. Because DEP effectively maps biophysical properties into a translational force whose direction and magnitude reflects cellular properties, some degree of separation occurs between particles of different characteristics. While DEP has been used on a microscopic scale to separate bacteria from erythrocytes (Markx et al., 1994), viable from nonviable yeast cells (Wang et al., 1993), and erythroleukemia cells from erythrocytes (Huang et al., 1992), the differences in the electrical polarizabilities of the cell types in those various mixtures were greater than those to be expected in many typical cell sorting applications.

Field flow fractionation (FFF) has also been generally employed for separation of matter, utilizing particle density, size, volume, diffusivity, thickness, and surface charge as parameters (Giddings, 1993). The technique can be used to separate many different types of matter, from a size of about 1 nm to more than about 100 micrometers which may include, for example, biological and non-biological matter. Separation according to field flow fractionation occurs by differential retention in a stream of liquid flowing through a thin channel. The FFF technique combines elements of chromatography, electrophoresis, and ultracentrifugation, and generally FFF requires the presence of a field or gradient to develop a differential flow. This differential flow creates a flow profile which may be, for example, linear or parabolic. A field is then applied at right angles to the flow and serves to drive the matter into different displacements within the flow profile which travel at differing velocities. Fields may be based on sedimentation, crossflow, temperature gradient, centrifugal forces, and the like. The technique suffers, however, from producing insufficiently pure cell populations, being too slow, or being too limited in the spectrum of target cells or other matter.

Thus, there exists a need in the art for highly discriminate characterization or identification of particulate matter, especially biological matter, that operates without physically modifying the structure of the matter to be separated. Moreover, such an approach should allow for the sensitive manipulation of such particles, which may include characterization and purification of desired matter from extraneous or undesired matter.

SUMMARY OF THE INVENTION

The present invention seeks to overcome drawbacks inherent in the prior art by combining the use of frequency-dependent dielectric and conductive properties of particles with the properties of the suspending medium. As used herein, the term "matter" is intended to include particulate matter, solubilized matter or any combination thereof. The invention provides a novel apparatus and novel methods by which different particulate matter and solubilized matter may be identified and selectively manipulated. These particles may also be collected by changing the DEP force or the fluid flow characteristics. Utilizing the invention in this manner, particulate matter and solubilized matter may be discriminated and separated. The apparatus and methods of the present invention may discriminate different types of matter simultaneously.

The present invention provides a method and apparatus for the discrimination of particulate matter and solubilized matter of different types. This discrimination may include, for example, separation, characterization, differentiation, isolation and manipulation of the matter. According to the present invention, the particulate matter may be placed in liquid suspension before input into the apparatus. The discrimination occurs in the apparatus, which may be a thin, enclosed chamber. Particles may be distinguished, for example, by differences in their density, size, dielectric permittivity, electrical conductivity, surface charge, and/or surface configuration.

The methods according to the present invention may be used to discriminate particulate matter, including inorganic matter, such as mineral, crystalline, colloidal, conductive, semiconductive or insulating particles and gas bubbles. The methods of the present invention may also be used to discriminate biological matter, such as cells, cell aggregates, cell organelles, nucleic acids, bacteria, protozoans, or viruses. Further, the particulate matter may be, for example, a mixture of cell types, such as fetal nucleated red blood cells in a mixture of maternal blood, cancer cells such as breast cancer cells in a mixture with normal cells, or cells that have been parasitized, such as red blood cells infested with malarial parasites. Additionally, the methods of the present invention may be used to discriminate solubilized matter such as a molecule, or molecular aggregate including, for example, proteins, or nucleic acids.

Particles to be discriminated may be of any size. However, the present invention is generally practical for particles between ~10 nm and ~1 mm, and may include, for example, chemical or biological molecules (including proteins, DNA and RNA), assemblages of molecules, viruses, plasmids, bacteria, cells or cell aggregates, protozoans, embryos or other small organisms, as well as non-biological molecules, assemblages thereof, minerals, crystals, colloidal, conductive, semiconductive or insulating particles and gas bubbles. For biological applications using living cells, the present invention allows cells to be separated without the need to alter them with ligands, stains, antibodies or other means. Cells remain undamaged, unaltered and viable during and following separation. Non-biological applications similarly require no such alteration. It is recognized however, that the apparatus and methods according to the present invention are equally suitable for separating such biological matter even if it has been so altered.

The apparatus may include, for example, a chamber. The chamber may have at least one inlet and one outlet port, an interior surface and an exterior surface. Alternately, the chamber may be constructed so that it is sealed upon introduction of matter. The chamber may further be designed to have structural characteristics which cause a fluid or gas traveling through the chamber to travel at differing velocities according to a velocity profile. The chamber may be circular in shape and may include, for example, a top wall, bottom wall, and a peripheral side wall. Alternately, the chamber may be rectangular in shape and may include, for example, a top wall, bottom wall and side walls. In selected embodiments, the chamber may be constructed so that the top wall and bottom wall are of a much greater magnitude than the peripheral side wall or other side walls, thereby creating a thin chamber capable of creating a velocity profile. Alternately, the chamber may be of other construction, such as triangular, rectangular, hexadecagonal, or other geometrical shapes. As such, the present invention is not intended to be limited to a particular geometric shape. The chamber according to the present invention may be constructed of many different materials, for example, glass, polymeric material, plastics, quartz, coated metal, electroplated ceramic, or the like.

The chamber includes at least one electrode element adapted along a portion or all of the chamber. Each of these one or more one electrode elements may be electrically connected to an electrical conductor. In the discussion which follows, the terms "electrode element" or "electrodes" will be used. As used herein, "electrode element" is a structure of highly electrically-conductive material. An electrical signal generator, which may be capable of varying voltage, frequency, phase or any combination thereof, may transmit at least one electrical signal to the electrode elements. The electrode elements of the present invention may include, for example, a plurality of electrode elements which may be connected to a plurality of electrical conductors, which in turn is connected to the electric signal generator.

The chamber according to the present invention may include a plurality of electrode elements which comprise an electrode array. As used herein, an "electrode array" is a collection of more than one electrode element in which each individual element may be displaced in a well-defined geometrical relationship with respect to one another. This array may be, for example, a spiral electrode array. As used herein, the term "spiral" encompasses an array in which individual electrode elements are concentrically arranged such that each individual electrode element originates at a periphery of the array and terminates at or near a center of the array. The shape of this spiral electrode array may be, for example circular, triangular, rectangular, hexagonal or any other appropriate geometric shape. This spiral electrode array may be a parallel spiral array, which means that individual electrode elements of the array maintain uniform distance from each adjacent electrode element. Further, the array may be comprised of microelectrodes of a given size and shape, such as an interdigitated array. The electrode array may be adapted along any interior or exterior surface of the chamber. Alternately, it is envisioned that the electrode array may be incorporated into the material which comprises the chamber walls. Further, the present invention may have a plurality of electrode arrays which may be adapted, for example, on opposing surfaces of the chamber. However, it may be possible to place the plurality of electrode arrays on adjacent surfaces or on all surfaces of the chamber.

Other configurations of electrode elements are contemplated by the present invention, such as electrode elements adapted at angles to the chamber. It is also possible to use a three-dimensional electrode element that may or may not be attached to the surface of the chamber. For example, electrode elements may be fabricated from or on silicon wafers, as is known in the art. If the electrodes are adapted along the exterior surface of the chamber, it is envisioned that a means of transmitting energy into the chamber, such as a microwave transmitter may be present.

When the electrode elements are energized by at least one electrical signal from the electrical signal generator, the electrode elements thereby create a spatially inhomogeneous alternating electric field, which may cause a DEP force on the particulate matter and solubilized matter causing it to move towards or away from regions of high electrical strength. This DEP force may be a conventional DEP force (cDEP), which may act in different directions with respect to the fluid, depending on the configuration of the electrode elements. The cDEP force typically acts in a direction substantially normal to the electrode element plane, that is, the cDEP force typically forces matter towards or away from this plane. In certain embodiments, the DEP force may act predominantly in a direction normal to this plane. However, the direction of the DEP force may be for example, vertically, sideways, or in another direction with respect to the electrode plane. By effect of this DEP force, the particulate matter and solubilized matter may be displaced to positions within the chamber. This displacement may be relative to the electrode elements, or may relate to other references, such as the chamber walls or spiral center.

The ratio of electrode element width to electrode element spacing may be modified to change the particulate matter and solubilized matter levitation height. That is, as used herein, "levitate" or "levitation height" means that matter is displaced at different levels with respect to the electrode elements, in any direction. Specifically, by changing this ratio, the electric field which is created is thereby altered. When the electric field is thereby altered, in magnitude and/or inhomogeneity, the levitation height of the matter similarly changes. This levitation need not be in a vertical direction, and may include displacement in a horizontal direction, for example. It is to be noted that a change in voltage may also cause a change in levitation height.

In the present invention, the cDEP force is dependent on the magnitude of the spatial inhomogeneity of the electric field and the in-phase (real) part of the electrical polarization induced in matter by the field. It is to be understood that the term "electrical polarization" is related to the well-known Clausius-Mossotti factor, described below. This field-induced electrical polarization is dependent on the differences between the dielectric properties between the matter and the suspending medium. These dielectric properties in general are represented by dielectric permittivity and electrical conductivity. The combination of these two properties is known as complex permittivity. The CDEP force causes the matter to move towards or away from regions of high electrical field strength, which in an exemplary embodiment, may be towards or away from the electrode plane.

The equation for the time-averaged conventional dielectrophoretic force in an electric field strength having an rms value of $E_{rms}$ is:

$$F(t)=2\pi\epsilon_m r^3 Re[f_{cm}]\nabla E_{rms}^2 \qquad (1)$$

where the factor $f_{cm}$ is the well-known Clausius-Mossotti factor defined as $f_{cm}(\epsilon_p^*,\epsilon_m^*)=(\epsilon_p^*-\epsilon_m^*)/(\epsilon_p^*2\epsilon_m^*)$, and where $\epsilon_p^*$ and $\epsilon_m^*$ are the complex permittivities of the matter and its suspending medium, respectively. The Clausius-Mossotti factor may also include other terms to account for other forms of electrical polarization or conductivity induced or modified by the applied field, for example, the surface charge of the matter. In the force equation, r is the radius of the matter desired to be discriminated, $Re[f_{cm}]$ is the real part (in-phase component) of the factor $f_{cm}$, and $\nabla E_{rms}^2$ is the magnitude non-uniformity factor of the applied electric field. As seen from equation (1), if the in-phase part of the Clausius-Mossotti factor is greater than zero, then the force is greater than zero, and matter tends to move towards the strong field. If the in-phase part of the Clausius-Mossotti factor is less than zero, the matter tends to move towards the weak field.

In an alternate embodiment of the present invention, the electrode array may include at least three sets of electrode elements. As used herein, "set" is a group of individual electrode elements having a defined geometric relationship to each other. Such a defined geometrical relationship may include, for example, a triangle, circle, square, spiral, or complex shapes such as conic sections, fractals, and the like. It is to be understood that sets of electrode elements may be designed based on principles of electromagnetic theory. At least one applied electrical signal having different phases may be applied to the at least three sets of electrode elements. For example, one applied signal may be adequately delayed by a capacitor or other time delay circuitry to provide each of the at least three sets of electrode elements a signal having a different phase. Alternatively, different signals having different phase relationships may be provided to the electrode elements. These signals thus create an electric field distribution that may be spatially inhomogeneous with respect to magnitude, and may travel through space by virtue of the phase distribution.

It is noted that by applying at least one electrical signal having different phases to the at least three sets of electrode elements, a traveling wave dielectrophoretic(twDEP) force is created in addition to the cDEP force. The twDEP force is dependent upon the phase distribution of the applied electric field (reflecting its movement through space, which is in the direction of small phase regions), and the out-of-phase (imaginary) part of the electrical polarization induced in the matter by the field. The twDEP force causes the matter to move towards or away from the direction of increasing phase values. The twDEP force typically acts in a direction substantially parallel to the electrode element plane. In the case of twDEP, the equation for the time-averaged traveling wave dielectrophoretic force is:

$$F(t)=2\pi\epsilon_m r^3 Im(f_{cm})(E_{x0}^2\nabla\Phi_x+E_{y0}^2\nabla\Phi_y+E_{z0}^2\nabla\Phi_z) \qquad (2)$$

where $Im(f_{cm})$ is the imaginary part (out-of-phase component) of the factor $f_{cm}$, and $E^2\nabla\Phi$ is the phase non-uniformity factor (where $E_{x0}$, $E_{y0}$ and $E_{z0}$ are the magnitudes of each electric field component in the Cartesian co-ordinate frame, and $\Phi_x$, $\Phi_y$, and $\Phi_z$, are the phases of each field component). As seen from Equation (2), if the out-of-phase part of the Clausius-Mossotti factor is greater than zero, the force directs matter towards regions where the phases of the field components are larger. If the out-of-phase part of the Clausius-Mossotti factor is less than zero, the force directs matter towards regions where the phases of the field components are smaller.

The combination of the cDEP and twDEP forces is referred herein as generalized dielectrophoresis (gDEP). The combination of equations (1) and (2) therefore results in the equation for the time-averaged generalized dielectrophoretic force:

$$F(t)=2\pi\epsilon_m r^3 (Re[f_{cm}]\nabla E_{rms}^2+Im(f_{cm})(E_{xo}^2\nabla\Phi_x+E_{yo}^2\nabla\Phi_y+E_{zo}^2\nabla\Phi_z)) \qquad (3)$$

Thus, matter under the influence of one or both of these forces may be displaced to different positions within the chamber. It is noted that the cDEP force may be approximately four times greater than the twDEP force caused by the same electrical field strength. It is to be understood that cDEP and twDEP are principal components of gDEP, and other gDEP forces such as a combination of cDEP and twDEP, may also act on matter in an apparatus according to the present invention. It is to be noted that the above equations are based on the so-called dipole approximation for the field-induced polarization in the particles. It may also be possible to exploit higher order poles induced in the particles.

In an embodiment according to the present invention, the electrode array may be a spiral electrode array. The spiral electrode array may comprise of at least three of spiral elements which may be adapted on the interior walls of a thin chamber. Specifically, the array may be placed on the top and/or bottom walls of the chamber, however it is noted that in other embodiments, the array may be placed on peripheral walls, or any other portion of a chamber. The geometry of the spiral electrode array may describe a circle, oval, rectangle, pentagon, or other geometrical shapes. The array may be designed such that individual elements originate at a periphery of the spiral, and terminate in a center. At least one alternating electrical signal may be applied to the elements of the spiral array at different phases, which thereby generates alternating electrical fields that are not only spatially inhomogeneous with respect to field strength but also travel through space by virtue of phase distributions.

As a result of these inhomogeneous characteristics of field magnitude and phase, cDEP and twDEP forces may be imposed on matter in the chamber in accordance with its dielectric and conductive properties, as well as the properties of a carrier medium. As discussed above, the cDEP component depends on the spatial inhomogeneity of the field strength and the in-phase (real) part of the field-induced polarization of the matter and causes it to move towards or away from regions of high electrical field strength. The twDEP component depends upon the phase distribution of the applied electric field (reflecting its movement through space) and the out-of-phase (imaginary) part of the induced polarization of the matter. This component may cause matter to move in the same or opposite direction to that of increasing phase values.

In an embodiment incorporating spiral electrode arrays, electric fields may be generated in which strong electric fields occur at the edges and in close relation to the electrode elements. The electric field decays with the distance from the electrode plane. Further, because of the relatively small thickness of the electrode elements, generally on the order of 0.1 to 10 $\mu$m for cellular applications, fringing effects result in a non-uniform distribution of electric field strength in a plane parallel to the electrode plane. Phase values of the field components may increase or decrease with increasing distance from the center of the spiral electrode array. Such electrical field distributions induce cDEP force components that move matter towards or away from the electrode array plane, (matter levitation) and twDEP force components that direct matter towards or away from the center or peripheral regions of the spiral electrode arrays (radial motion). Thus, depending on the applied field frequency and the dielectric characteristics of matter and its suspending medium, the cDEP and twDEP force components may direct matter to the center or the peripheral regions of the electrode array, trap matter at the edges of the electrode elements, or levitate matter to different heights within the chamber.

A concentric ring model may be used for the analysis of the spiral electrode array. In this analysis, the electrical field is independent of the angular direction of the spiral and is dependent only on the radial distance from the electrode center and the height above the electrode plane. In such a case, the field magnitude non-uniformity factor, $\nabla E^2_{RMS}$, and field phase non-uniformity factor, $(E^2_{x0}\nabla\phi_x + E^2_{y0}\nabla\phi_y + E^2_{z0}\nabla\phi_z)$, generally of 3-D vector form, may be expressed by vectors containing only two non-zero components orientated in the radial and vertical directions, as shown in FIG. 9A and FIG. 9B for a chosen angular direction of $\theta=0$ (corresponding to a quarter of X-Z plane in a Cartesian coordinate frame with x>0 and z>0).

By definition, the magnitude non-uniformity factor $\nabla E^2_{RMS}$ always points towards the strong field regions. Thus, its vertical component points to the electrode plane and its radial component, having appreciable values only at heights below approximately 10 $\mu$m, points towards the nearest edge of the electrode elements. It follows that the cDEP force component, being proportional to $\nabla E^2_{RMS}$, can direct cells towards or away from the electrode plane in the vertical direction, but can only trap cells at or between the electrode edges, and is therefore unable to induce lateral cell motion over distances larger than one electrode width/gap period. However, above approximately 10 $\mu$m the phase non-uniformity factor $(E^2_{x0}\nabla\phi_x + E^2_{y0}\nabla\phi_y + E^2_{z0}\nabla\phi_z)$ has a negligible vertical component and a unidirectional radial component pointing away from the center of the spiral electrode array.

Below 10 $\mu$m, the factor exhibits comparable magnitudes in both its radial and vertical components and, furthermore, the direction of the radial component becomes reversed so that field components travel in the opposite direction to the applied traveling potential wave. It follows that the twDEP component, being proportional to $(E^2_{x0}\nabla\phi_x + E^2_{y0}\nabla\phi_y + E^2_{z0}\nabla\phi_z)$, results mainly in cell motion along the radial direction towards or away from the electrode center at high levitation positions, and induces complex cell behavior for levitation heights below 10 $\mu$m. The overall kinetic response of cells on the spiral electrode array results from the combined effects of the cDEP and twDEP force components. Thus, when the cDEP force is negative, cells will be levitated above the electrode plane and simultaneously transported towards the electrode center or periphery by the twDEP force. On the other hand, a large, positive cDEP force can trap cells at the electrode edges overcoming any twDEP force that is present.

As shown in FIG. 1 depending on the conductivity of the suspending medium and the applied field frequency, MDA231 cells exhibit four characteristic types of electrokinetic responses when they are subjected to dielectrophoretic forces generated by the spiral electrode array.

Levitation and Co-field Radial Motion: Cells are directed to the interelectrode regions, levitated to characteristic equilibrium heights above the electrode plane in several seconds, and exhibit slow co-field radial motion.

Levitation and Anti-field Radial Motion: Cells are not only levitated but also directed radially towards or away from the center of the electrode array. The cell motion direction is opposite to that of the traveling wave field. Each cell exhibits rotation about an axis through its center that is oriented normally to the radial direction and parallel to the electrode plane. Reversing the phase sequence of the voltage signals applied to the electrode elements results in reversal of the direction of cell radial motion and in the sense of cell rotation.

Transitional behaviors: Some cells are levitated and move towards the electrode center. Other cells remain close to the electrode surface and move towards the periphery. Still other cells are loosely trapped at the electrode edges where they exhibit fast rotation.

Entrapment: Cells are attracted towards the nearest electrode edge and trapped there, independently of their initial positions. Cells exhibit little or no rotation.

Governing Equations for Cell Electrokinetic Responses

Levitation

At the equilibrium levitation position, dielectrophoretic force in the vertical direction balances the cell sedimentation force so that:

$$-\frac{4}{3}\pi r^3(P_c - P_m)g + \overline{F}_{DEP} \cdot \overline{a}_z = 0, \qquad (4)$$

where $P_c$ and $P_m$ are the densities of cell and the suspension medium, and g is the gravitational force constant (9.8 m/s$^2$) and $a_z$ is a unit vector in the z direction. Ignoring the contribution of twDEP force component, the above equation can be reduced to:

$$2(P_c - P_m)g = 3Re(f_{cm})\nabla E^2_{RMS} \cdot \overline{a}_z. \qquad (5)$$

Thus cell levitation effects are determined by the relative cell density and dielectric property, and the field magnitude non-uniformity factor ($\nabla E^2_{RMS}$). Therefore, the following conclusions may be drawn:

For cells having negative buoyancy ($R_c > R_m$), negative cDEP forces (Re($f_{CM}$)<0) allow for a stable levitation of the cells.

To achieve levitation, the applied voltage V must exceed a threshold value, $$\sqrt{2(P_c-P_m)g/(3Re(f_{CM})\nabla E^2_{ORMS\ z=r} \cdot \overline{a}_z)} \text{ . where } \nabla E^2_{ORMS} = \nabla E^2_{RMSV=1}.$$

Since $\nabla E^2_{0RMS} \cdot \bar{a}_z$ decreases monotonically with distance from the electrode plane, cells will be levitated to higher equilibrium position with increasing V and Re($f_{CM}$).

Cell radial motion

The cell kinetic behavior in the radial direction is controlled by the radial components of DEP force and the opposing Stokes' drag, as $$\frac{4}{3}\pi r^3 Pc \frac{dV_\chi}{dt} = F_{DEP} - 6\pi\eta V_\chi. \quad (6)$$

where $V_x$ is the cell velocity, $\eta$ is the dynamic viscosity. For a typical cell radius r<10 μm and motion velocity $V_r$<100 μm/sec, the cell Reynolds number is <0.1. In such a heavily damped dynamic system, the instantaneous velocity is proportional to the applied instantaneous DEP force and is given by $$V_r = \frac{F_{DEP r}}{6\pi r\eta} \quad (7)$$

$$Vr = \frac{\epsilon_m r^2}{3\eta}(Re(f_{CM})\nabla E^2_{RMS} + \\ Im(f_{CM})(E^2_{\chi 0}\nabla\Phi_\chi + E^2_{y0}\nabla\Phi_Y + E^2_{z0}\nabla\Phi_z)) \quad (8)$$

Thus:

The instantaneous velocity is proportional to the instantaneous DEP force acting on the cell.

For cells having similar dielectric properties, larger cells move faster than smaller ones.

The phase non-uniformity factor decays rapidly with the distance from the electrode plane.

Cell motion velocity is therefore influenced by the cell equilibrium levitation position, which is dependent on the parameter Re($f_{CM}$). It is the interplay between Re($f_{CM}$) and Im($f_{CM}$) that determines the induced cell velocity in the radial direction.

Based on Eq. 7, the time-averaged cell velocity can be written in terms of the applied voltage U as $$<V_x> = \frac{\epsilon_m r^2 U^2}{3\eta} Im(f_{CM}) F_0(z) \quad (9)$$

where the cDEP force term has been neglected. The factor $F_0(Z)$ corresponds to $(E^2_{x0}\nabla\phi_x + E^2_{y0}\nabla\phi_y + E^2_{z0}\nabla\phi_z)\cdot a_r$ for a unit applied voltage and it decreases with the height z for z > approximately 10 μm. Eqs. 5 and 9 indicate that increasing the voltage U will result in two competing effects on the cell radial velocity. The first is to increase $V_x$ according to $U^2$ dependence of Eq. 9, while the second is to lower $V_x$ through the decrease in $F_0(Z)$ resulting from greater levitation of the cell according to Eq. 5. The combination of these two effects together result in a net increase in the cell radial velocity with applied voltage, but at a rate slower than the voltage-squared dependence.

Electrode polarization effects

In the low frequency range (below approximately 20 kHz for a suspension conductivity of 56 mS/m), cell levitation height increases monotonically with frequency. The factor Re($f_{CM}$) attains a near-constant value of –0.5 in this frequency range due to the non-conductive cytoplasmic membrane. Thus according to the levitation balance Eq. 5, the frequency-dependency of cell height suggests that the parameter $\nabla E_0^2 \cdot a_z$ attains the same value at higher positions for higher applied frequencies. This frequency-dependent field distribution effect appears to be a direct result of electrode polarization. The equivalent circuit for the electrode system is shown in FIG. 10. FIG. 10 shows equivalent circuits for the electrode system of the present invention. The electrode polarization is characterized by the polarization capacitance ($C_{pol}$) 50 and resistance ($R_{pol}$) 55. The total polarization impedance is given by ($R_{pol}$–j/ω$C_{pol}$)). The impedance of the bulk solution is represented by the bulk capacitance ($C_{bulk}$) 60 and resistance ($R_{bulk}$) 65. The voltage applied to the bulk solution is smaller than that applied to the electrodes because of the voltage drop across the electrode polarization impedance.

In order to determine the voltage applied to the bulk solution, the impedance of the whole electrode system may be measured as a function of the field frequency and fit the data to several mathematical models of polarization impedance. For example, a model developed by Warburg based on diffusion considerations (Schwan, 1992), states that the polarization capacitance and resistance are both proportional to $f^{0.5}$ and that the impedance has a frequency-independent phase angle of 45°. Other models include various modifications of the Debye-dispersion equation for the polarization impedance, adopted by Jaron el al. (1968) and Buck (1992). Perhaps surprisingly, the relative difference for the frequency-dependent polarization impedances derived using these different models is less than 15% for the frequency range investigated, indicating an inherent consistency between these models. Thus, both the bulk solution and the frequency-dependent polarization impedances may be deduced, and the true voltage applied to the bulk solution may be calculated. The above-described electrode polarization effect was taken into account in the theoretical analysis of both cell levitation height and radial velocity described above.

Common electrical conductors may be used to connect the one or more sets of electrode elements to the signal generator. The common electrical conductors may be fabricated by the same process as the electrodes, or may be one or more conducting assemblies, such as a ribbon conductor, metallized ribbon or metallized plastic. A microwave assembly may also be used to transmit signals to the electrode elements from the signal generator. It is envisioned that such a configuration may require presence of a ground plane. More typically, alternating electrodes along an array may be connected so as to receive different signals from the generator.

The electrical generator may be capable of generating signals of varying voltage, frequency and phase and may be, for example, a function generator, such as a Hewlett Packard generator Model No. 8116A. Signals desired for the methods of the present invention are in the range of about 0 to about 15 volts, and about 0.1 kHz to about 180 MHz, and more preferably between about 0 to about 5 volts, and about 10 kHz to 10 MHz. These frequencies are exemplary only, as the frequency required for matter discrimination is dependent upon the conductivity of, for example, the suspension medium. Further, the desired frequency is dependent upon the characteristics of the matter to be discriminated. The discrimination obtained depends on the shape, size and configuration of the electrode elements, for example. In an exemplary embodiment, the signals are sinusoidal, however it is possible to use signals of any periodic or a periodic waveform. The electrical signals may be developed in one or more electrical signal generators which may be capable of varying voltage, frequency and phase. It is to be noted that a signal generator may be fabricated that is integral to the chamber and electrode assembly. Such a signal generator may be manufactured by known semiconductor methods, and which may be external or internal to the chamber walls.

An embodiment incorporating a spiral electrode array may include, for example, four separate spiral electrode elements. Each of the elements may be energized with an electrical signal in phase quadrature.

A chamber according to the present invention may have at least one inlet and outlet port. These ports may be the same port, or the chamber may be constructed to have different ports. In an embodiment in which these ports are the same port, the port may be located within a central portion of a spiral array. Alternately, it may be possible to provide for a plurality of inlet and/or outlet ports on the side or peripheral walls. In addition to the at least one inlet port and one outlet port, the chamber may also include one or more input ducts which allow the fluid to flow through the apparatus.

The outlet port of the chamber according to the present invention may take many forms. Specifically, the outlet port may be a single port, or a plurality of ports, or an array of ports. The outlet port, for example, may be located along the entire periphery or a part of the periphery of the chamber. The outlet port may be adapted to receive matter of various shapes and sizes. For example, the size of the outlet port may vary from approximately twice the size of the matter desired to be discriminated to the entire width of the chamber. In one embodiment, the outlet port may be constructed of one or more tubing elements, such as TEFLON tubing. The tubing elements may be combined to provide an outlet port having a cross section comprised of individual tubing elements.

Further, for example, the outlet port may be connected to fraction collectors or collection wells which are used to collect separated matter. As used herein, "fraction collectors" and "collection wells" include storage and collection devices for discretely retaining the discriminated particulate and solubilized matter. Other components that may be included in the apparatus of the present invention are, for example, measurement or diagnostic equipment, such as cytometers, lasers, particle counters and spectrometers. In one embodiment, a central outlet port may be located in the center of a spiral electrode array. A sensing element, which may be a biosensor/detector may be placed in close proximity to this central outlet port to automatically detect the presence of a particular type of matter.

It may be possible to introduce a fluid into the chamber from a central inlet port (or any other inlet port) which travels in a radially outward manner. This flow may thereby aid in transporting matter to the periphery of the spiral array. The fluid flow may be according to a velocity profile. This velocity profile may be, for example, a hydrodynamic fluid profile such as a parabolic flow profile. The velocity profile may be determined by knowing the flow rate of the fluid, and the chamber size. The average velocity may then be calculated according to the equation:

$$\text{average velocity} = (\text{flow rate}) / (2\pi \times r \times \text{chamber thickness}). \quad (10)$$

where r is the distance from the center of the spiral. Parameters that determine the velocity profile of the fluid flow include (but are not limited to): the chamber width or thickness; constrictions or expansions of the fluid flow path which may include, for example, those arising for a non-parallel disposition of opposing chamber walls, or from the presence of suitably-placed obstructions or vanes; surface roughness of the chamber walls; structural features of the chamber walls that give rise to periodic or a periodic modifications of the thickness of the fluid stream, including the electrode elements and other surface structural configurations, and the geometrical form of the chamber which may be, for example, rectangular, circular, wedge-shaped, stepped, or the like.

Embodiments of the present invention may have, for example, one inlet port adapted to receive the particulate matter to be discriminated. The inlet port may be located, for example, on the top or bottom of one end or center or any other position within the chamber. This apparatus may also include one or more ducts to introduce an externally applied fluid-flow that travels through the chamber. The ducts may be located near the inlet or outlet ports, or may be located along a periphery wall, or any other portion of a chamber. The introduced fluid may be used to facilitate removal or displacement of matter from or within the spiral electrode region. Following transit through the chamber, fluid leaves at the opposite end. This exit end of the chamber may include, for example, one or more exit ports, which may be arranged in one or more arrays of exit ports.

Different electrical signals (frequency or magnitude or both) may be applied to different electrode elements. There is a synergistic interaction between these different electrical signals which creates an inhomogeneous electric field. Different matter equilibrates at different characteristic distances from the electrode arrays based on this synergistic interaction of the differing electrical signals, herein an "equilibrium position." The equilibrium position is therefore caused by cDEP forces on the particles. Additionally, twDEP forces may impact this equilibrium position. This equilibration position depends on the dielectric and conductive properties of the matter, the magnitude and frequency of the electrical fields applied to the electrodes on the opposing chamber walls, fluid density, viscosity, and dielectric properties. The equilibrium position of matter depends on the synergism of the different electrical signals acting within the chamber to levitate the matter.

Discrimination may be accomplished either in "batch mode" or in "continuous mode." In batch mode, an aliquot of particles is injected and electrical signals driving the electrodes are chosen so as to move a target subpopulation within the injected aliquot to the center of the spiral and to simultaneously either trap other particle types on the electrode or else move them to the periphery of the chamber. In continuous mode, a constant stream of particles is injected into the inlet port, and only target particles are trapped on spiral electrodes. Other particles emerging from the periphery are continuously collected.

A further embodiment of the chamber having two facing electrode arrays adapted on opposing surfaces is also possible. In this design, the electrode arrays are arranged along the opposing surfaces so that the individual electrode elements of the facing arrays are substantially parallel to each other. However, it may be possible to create the desired DEP forces by electrodes perpendicular or in other directions to each other. Different electrical signals (frequency, magnitude, and phase, or a combination thereof) may be applied to the facing electrodes from the signal generator so that particles experience different cDEP and/or twDEP forces. The cDEP forces may act to displace matter to or away from the electrode planes, based on the magnitude of the field inhomogeneity. The twDEP forces may act in a plane substantially parallel to the electrode arrays, based on the phase inhomogeneity of the field produced by the electrode arrays.

The cDEP forces in combination with gravitational effects cause matter to be displaced characteristic distances with respect to the electrode arrays. This characteristic distance is a function of the matter's dielectric and conductive properties, the magnitude and frequency of the electrical fields applied to the electrodes on the facing chamber walls, and the fluid density, viscosity and dielect properties. Matter therefore equilibrates at an equilibrium position with respect to the electrode arrays dependent on these characteristics.

To further achieve the benefits of discrimination, the carrier fluid characteristics at different vertical displacements may be varied by modifying for example, flow rate, fluid density, viscosity, dielectric permittivity, pH and conductivity of the carrier fluid. In this way, additional matter characteristics may be exploited for particular discrimination applications.

Prior techniques for characterizing a particle's dielectric properties include classical dielectric impedance measurement of particle suspension, conventional dielectrophoresis (cDEP) in A.C. electric field of inhomogeneous strength, electrorotation (ROT) of matter in rotating electric fields, and traveling-wave dielectrophoresis (twDEP) in a traveling electric field. Classical dielectric impedance measurements of particle suspensions may be employed to deduce averaged dielectric values for many matter types. However, the sensitivity of the technique is limited and it cannot operate on individual types of matter. Measurements of particle kinetic behaviors using cDEP, twDEP and ROT methods can provide dielectric information for individual matter. Nevertheless each of these methods is related to either the in-phase (real) or out-of-phase (imaginary) part of the induced polarization (cDEP: the in-phase part; twDEP and ROT: the out-of-phase part). The electrokinetic behaviors of matter on the spiral electrode array of the present invention depend on both the in-phase and out-of-phase part of the induced polarization. Consequently, the determination of the particle's dielectric characteristics is complete and derived from the total information regarding the induced polarization. The present invention represents the first time a particle's dielectric characteristics have been deduced from electrokinetic measurements of both in-phase and out-of-phase components of the induced polarization. This approach allows for more accurate characterization of individual matter.

There are several limitations in applying cDEP forces alone for manipulating matter:

cDEP forces are proportional to inhomogeneity in the field strength. Except for the so-called isomotive electrode design, the field inhomogeneity varies spatially and the cDEP forces acting on matter therefore depend on particle positions. This limits the discriminatory ability of selective cDEP manipulation of matter.

Microelectrode arrays, such as polynomial electrodes, have been shown to be capable of concentrating matter to an isolated electrical field minimum through negative cDEP effects. However electric signals of very large magnitude are needed to collect matter on a relatively large (~mm) electrode scale. Periodic microelectrode arrays such as interdigitated, castellated electrodes are effective in generating field inhomogeneities over a large area but they cannot concentrate matter in a single specific region.

Particle cDEP behaviors are predetermined by the electric field distribution of a given electrode geometry, and little control can be exerted through changing applied electrical signals. Furthermore particle dipole-dipole interactions in a cDEP field tend to attract matter to form pearl-chains, negatively impacting particle selectivity.

Chambers have been constructed of linear electrodes using twDEP manipulation generated by a traveling electric field, but it is ineffective for achieving large scale manipulations. Furthermore it cannot be used for focusing or isolating target particle types to specific regions.

The present invention makes use of both cDEP and twDEP force components by generating an electrical field distribution with a spiral electrode array. It exploits the inhomogeneous distribution in both field strength and field phase values, and utilizes both in-phase and out-of-phase components of the induced particle polarizations. These new features allow for high selectivity for manipulating matter of different types. Furthermore, the present invention allows for a relative constant traveling force to be generated that directs target matter to the central region of the electrode array. It does not require a very large voltage to generate twDEP force components across a large working area. Compared to previous cDEP manipulations, particle dipole-dipole interactions are much less influential in the electrical fields generated by the spiral arrays.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A–3F show the frequency dependency of individual cells in a spiral electrode array.

DESCRIPTION OF ILLUSTRATIVE EMBODIMENTS

Figure 1:
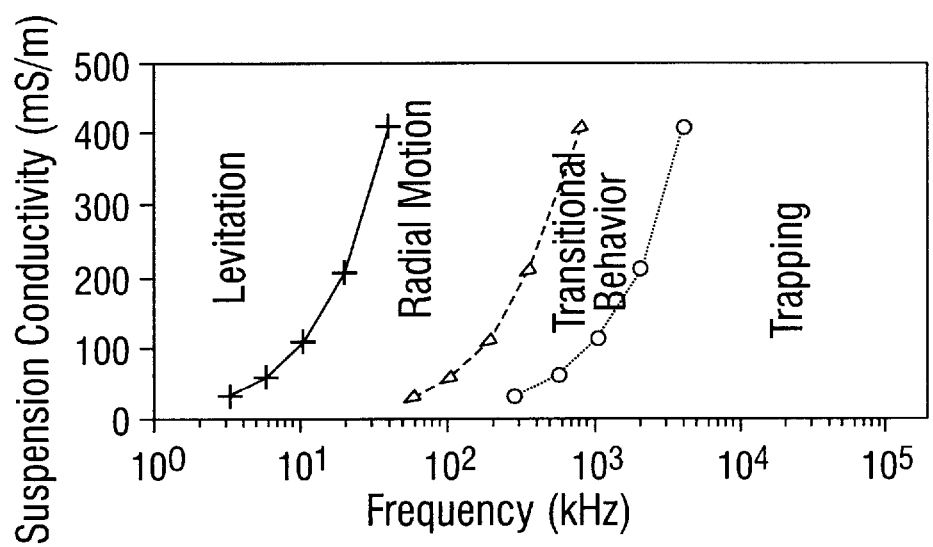
FIG. 1 is a map of the electrokinetic responses of MDA231 cells to DEP forces of different frequencies.

The following examples are included to demonstrate illustrative embodiments of the invention. It should be appreciated by those of skill in the art that the apparatus and techniques disclosed in the examples which follow represent devices and techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. While the following examples use the term particle, the skilled artisan will realize that the present apparatus and methods are suitable to solubilized matter as well.

In an illustrative embodiment, the chamber may be constructed in many shapes. For example, a rectangular shape using two glass slides as chamber walls may be used. These chamber walls may be spaced apart by spacers to create the rectangular design. These spacers may be made of, for example, glass, polymeric material such as TEFLON, or any other suitable material. Alternately, an O-ring structure may be used to provide the peripheral walls of the chamber. The size of the chamber and spacing between chamber walls is dependent on the size of the particles which are to be discriminated. To practice the methods of the present invention, an apparatus may have spacing between about 1 $\mu$m and about 1 mm, and more preferably between about 20 microns and about 200 microns in an illustrative embodiment for the purpose of discriminating mammalian cells. An apparatus according to the present invention can discriminate cells at a rate between about 1000 and about 3 million cells per second. Factors that determine discrimination rate include, for example, the dielectric properties of the particles to be discriminated, the electrode design, fluid flow rate, and frequency and voltage of the electrical signals. The chamber dimensions may be chosen to be appropriate for the input matter type, characteristics, and degree of discrimination desired or required.

In certain embodiments, one or more surfaces of the chamber may support an electrode array. The electrode array may be a microelectrode array of, for example, parallel spiral electrode elements. In certain embodiments, the electrode elements may be spaced about 20 microns apart and have a width of approximately 20 microns. The apparatus may accommodate electrode element widths of between about 0.1 microns and about 1000 microns, and more preferably between about 1 micron and about 100 microns for embodiments for the discrimination of cellular matter. Further, electrode element spacing may be between about 0.1 microns and about 1000 microns, and for cellular discrimination more preferably between about 1 micron and about 100 microns. Alteration of the ratio of electrode width to electrode spacing in the parallel spiral electrode design changes the magnitude of the dielectrophoretic force and thereby changes the particle levitation characteristics of the design. Electrical signals may be applied by more than one bus which provides the same or different electrical signals. In certain embodiments, alternate electrode elements may be connected to different electrode buses. In this configuration, alternate electrode elements are capable of delivering signals of different characteristics. As used herein, "alternate electrode elements" may include every other element of an array, or another such repeating selection of elements. The electrode elements may be fabricated using standard microlithography techniques that are well known in the art. For example, the electrode array may be fabricated by ion beam lithography, ion beam etching, laser ablation, printing, or electrodeposition. The array may be comprised of for example, a 250 nm gold layer over a seed layer of 100 nm chromium.

The selective manipulation of target matter type(s) may be achieved by two operational schemes where electrical field-induced dielectrophoretic forces are utilized (1) alone, or (2) in conjunction with additional, externally applied fluid flow forces. It may be desired for this manipulation to direct matter towards the central regions of the spiral electrode array. Alternatively, it may be desired for this manipulation to direct matter to the peripheral regions of the spiral electrode array. The basis for such selective manipulation is that different matter types possess different dielectric properties and experience different dielectrophoretic forces under the same electric field conditions.

In the scheme (1), the procedure may include application of appropriately chosen field conditions (frequency, magnitude and phase sequences of the electrical signals) so that (a) target matter type(s) experience(s) a twDEP force component that directs them towards the central regions of the spiral electrode array. Simultaneously, other matter types experience large positive cDEP forces that trap them at the electrode edges or, possibly, twDEP forces that direct them towards the peripheral regions of the electrode array. Alternatively, scheme (1) can be realized by a sequence of electrical signals. For example, first, a chosen field condition can be applied to trap target cell types at the electrode edges by cDEP forces whilst other matters are directed towards the peripheral regions of the electrode array by twDEP forces. Second, after all the "undesired" matters are removed from the spiral electrode regions to the periphery, the field conditions can be changed so that the remaining target matter types on the electrode spiral are concentrated at the spiral by twDEP forces.

In scheme (2), externally applied fluid flow forces are used to facilitate removal of "undesired" matter types from the spiral electrode region by introducing carrier medium from one or more additional inlet ports. In this case the electrical field and fluid flow conditions are first adjusted so as to trap target matter types under the influence of positive cDEP while the "undesired" matter types are flushed out of the chamber even if they experience cDEP and twDEP forces. Second, after all the "undesired" matter is removed from chamber, the field conditions can be changed so that the remaining target matter types on the electrode spiral are concentrated at the spiral by twDEP forces. The dielectrophoretic forces acting on matter is dependent on its size, dielectric permittivity, electrical conductivity, surface charge, and/or surface configurations. Thus the matter manipulations described in this invention utilize these properties. Such selective manipulation is especially useful for the concentration and/or isolation of rare cell types from a mixture.

In the above descriptions of typical matter manipulations using the spiral electrode configuration, "undesired" matter types refer to those species to be removed from the electrode region. In some applications these "undesired" matters can be collected and utilized.

An apparatus according to the present invention may be used with various methods of the present invention. For example, an apparatus according to the present invention may be used in a method of discriminating or characterizing particulate matter and solubilized matter utilizing dielectrophoresis. This method includes the following steps. First, a carrier medium, such as a cell suspension medium, tissue culture medium, a sucrose solution, or the like, which may include the matter to be discriminated, may be introduced into one or more inlet ports of the chamber. At least one alternating electrical signal may be applied to the one or more electrode elements at different phases, which creates a traveling electric field, which may also be spatially inhomogeneous, within the chamber. As used herein, "different phases" means that adjacent electrode elements within an array may receive signals having different phases. However, many electrode elements may receive signals of the same phase. For example, four adjacent electrode elements may receive signals of 0°, 90°, 180° and 270° respective phase. The next four adjacent electrode elements may receive signals having this same phase relationship. Many other such phase relationships between electrode elements may be used, and the sequence and number of electrode elements which have the same phase may be varied.

The field created by the electrical signals causes the matter within the chamber to be displaced to positions within the chamber. Thus, the matter is discriminated according to its positions within the chamber. To further discriminate matter, the electrical signal may be varied (frequency, magnitude, phase or any combination thereof). Such a change thereby causes a change in the traveling alternating electric field which, in turn, changes the displacement of the matter.

The apparatus and methods of the present invention may be used for a number of different useful manners. For example, the methods according to the present invention may be used to determine characteristics of an unknown particulate matter and unknown solubilized matter in a sample of matter. These characteristics can then be compared to known matter. Additionally, the methods of the present invention may be used to diagnose a condition by determining a presence of unidentified particulate matter and unidentified solubilized matter in a patient sample. This unidentified matter may be, for example, the presence of a cancer, a virus, parasite, or the like. After determining the presence of a condition, the methods of the present invention may be used to treat the condition by using an apparatus according to the present invention to discriminate the cancer, virus, parasite or the like from normal blood or bone marrow cells.

"Manipulation" as used in relation to the present invention may include, for example, characterization, separation, fractionation, concentration and/or isolation. Typical biological applications for the device useful for specific products and services include the manipulation of tumor cells, such as epithelial tumor cells or leukemia cells, from blood and hemopoietic stem cells, purging of tumor cells from bone marrow and hemopoietic stem cells and mixtures with other normal cells, purging of residual T-lymphocytes from stem cells, and enrichment of specific target cell types including tumor cells, stem cells, etc. Also included is the manipulation of leukocyte cell subpopulations, removal and concentration of parasitized erythrocytes from normal erythrocytes in malaria and of other parasitized cells from their normal counterparts, manipulation of cells at different phases of the cell cycle, manipulation of viable and non-viable cells, manipulation of free cell nuclei, and manipulation of nucleated fetal erythrocytes from maternal blood for further analysis including genetic testing. Moreover, the invention contemplates the manipulation of bacteria, viruses, plasmids and other primitive organisms from water, blood, urine, cell mixtures and other suspensions, manipulation and identification of tumor cells in biopsies, plaques and scrape tests including Pap smears, and the manipulation and identification of metastatic tumor cells from cell mixtures.

With different and smaller electrode geometries, it is contemplated that the technology can be used for molecular applications including manipulation of DNA or RNA molecules and/or DNA or RNA fragments according to their molecular weight, folding characteristics and dielectric properties, manipulation of chromosomes, manipulation of specific protein/DNA and protein/RNA aggregates, manipulation of individual proteins from a mixture, and manipulation of specific subcellular molecular complexes and structures.

In order to optimize particle discrimination in different applications it is understood that the present invention may encompass use of specifically-targeted electrodes and chamber designs. These designs should provide a sensitive dependency of the height of particle levitation on the particle dielectric properties. For example, alteration of the ratio of electrode width to electrode spacing in the parallel electrode design changes the vertical component of the dielectrophoretic force and thereby changes the particle levitation characteristics of the design. Other strategies for providing improved particle discrimination include, for example, using more than two sets of electrode elements with different frequencies and/or voltages applied to them and the exploitation of synergism between electrical signals applied to electrode arrays on both the chamber bottom and top walls. In addition, dielectric (i.e. non-conducting) elements can be placed within the chamber to modify both the electrical field distribution and the hydrodynamic flow profile. The electrode element size and shape may be designed to optimize discrimination. Furthermore, several electrode geometries (energized with the same or different electrical signals) can be connected serially so as to provide for stepwise discrimination between different particulate matter and solubilized matter. Different chamber configurations can also be used in series.

EXAMPLE I

Figure 2A:
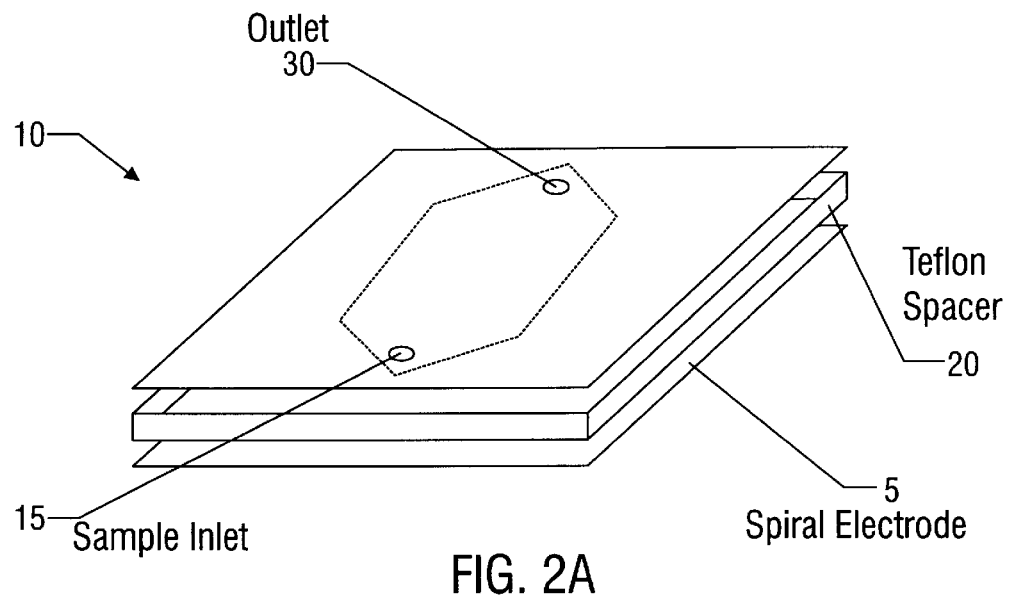
FIG. 2A is a block diagram of an apparatus according to the present invention.
Figure 2B:
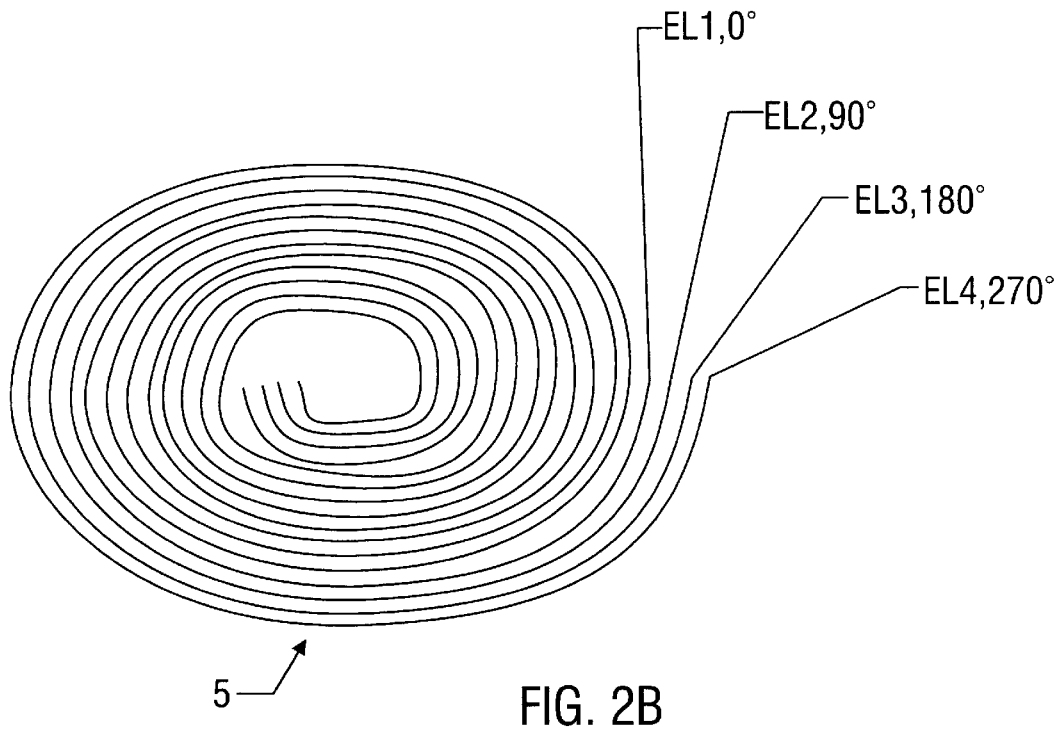
FIG. 2B is a block diagram of spiral electrode array according to the present invention.
Figure 3E:
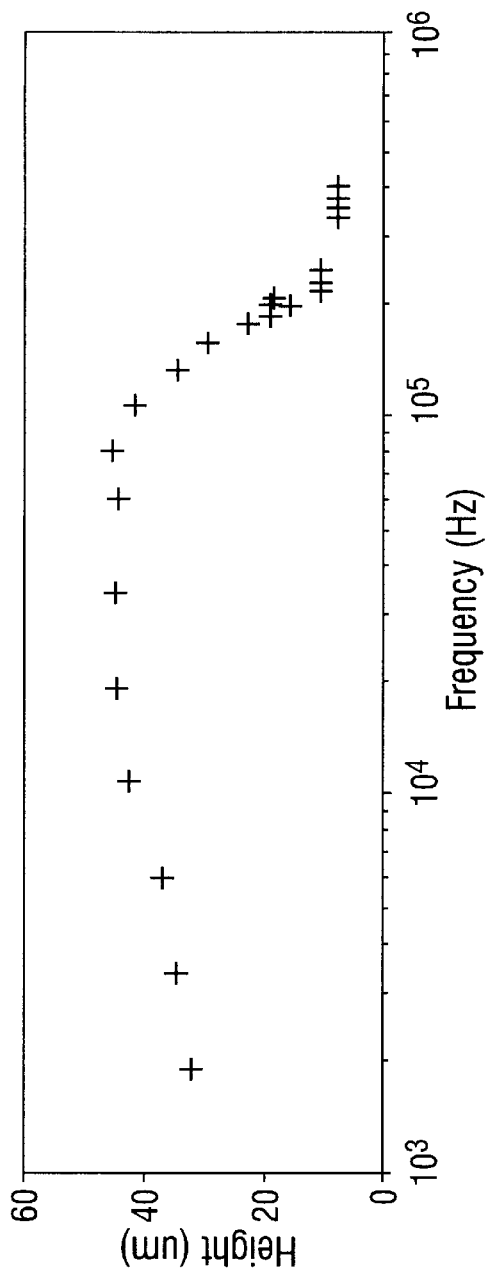
Figure 3F:
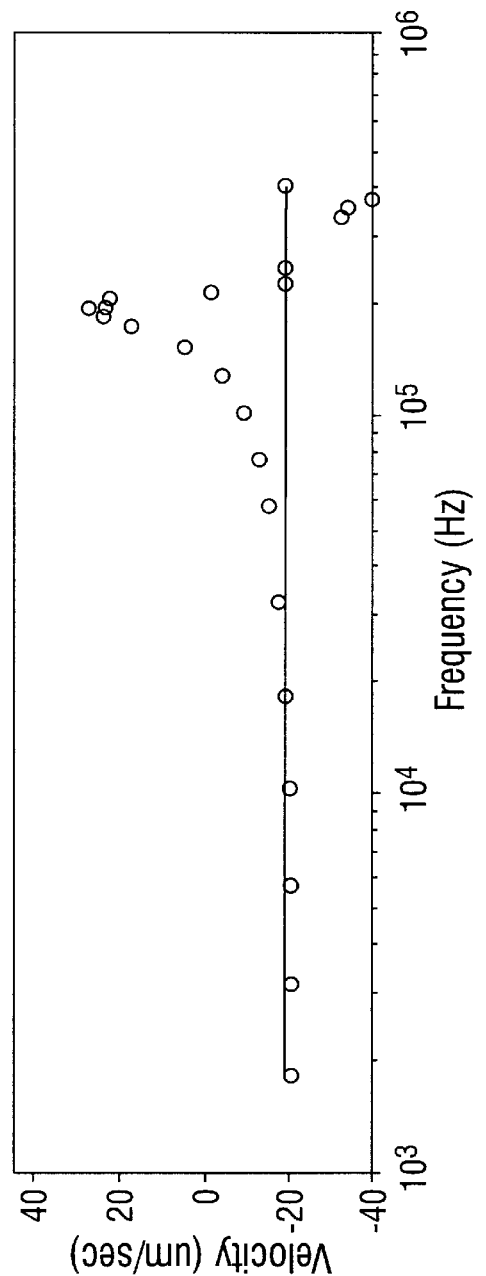
Figure 4B:
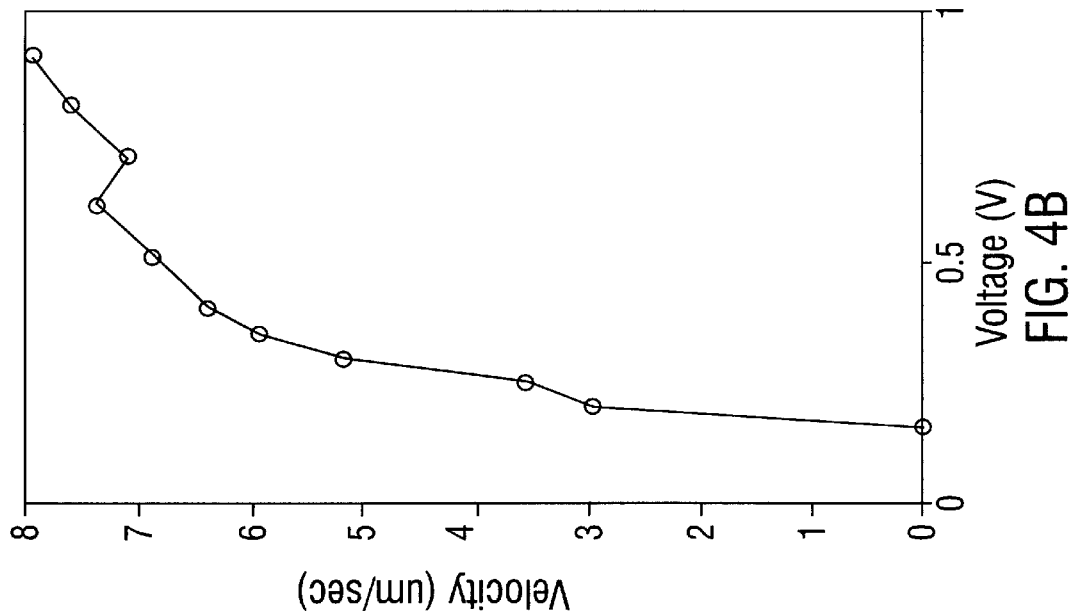
FIGS. 4A–4F show the voltage dependency of individual cells in a spiral electrode array.
Figure 4A:
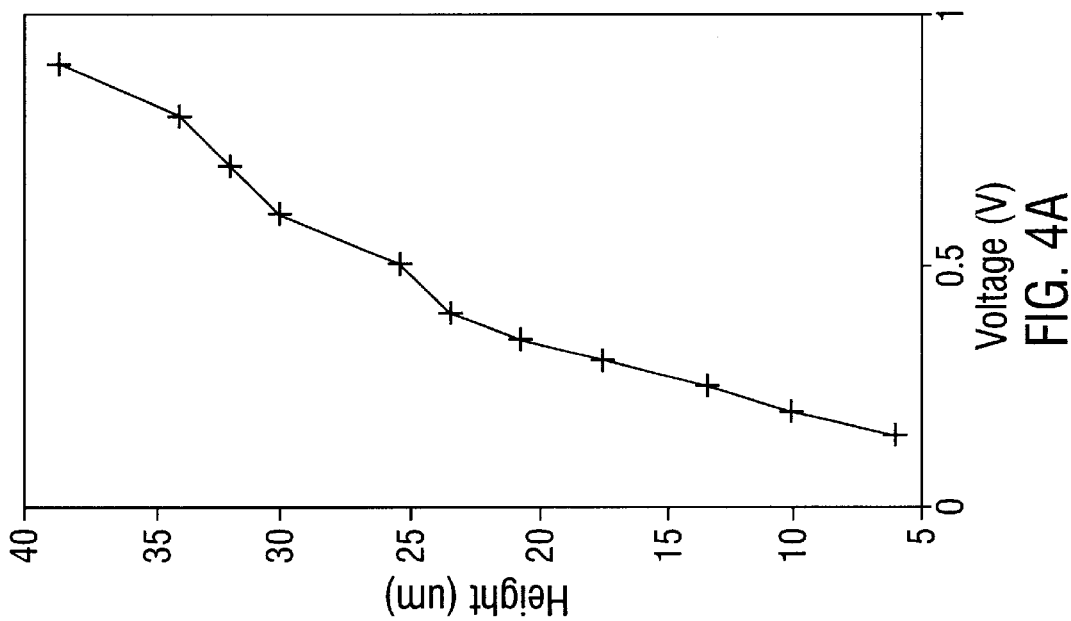
Figure 4D:
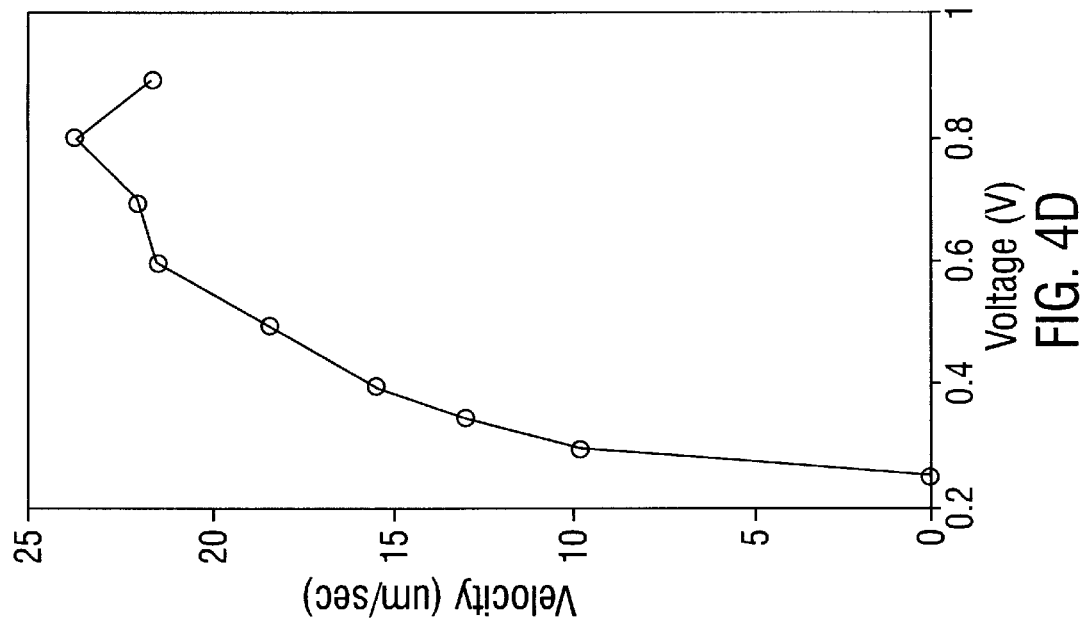
Figure 4C:
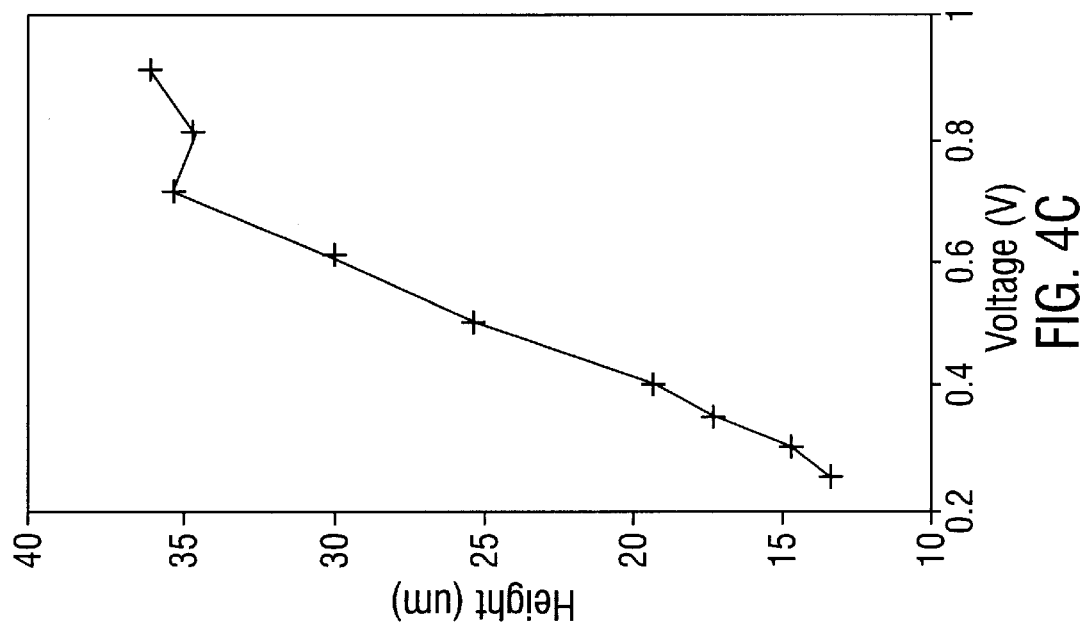
Figure 4F:
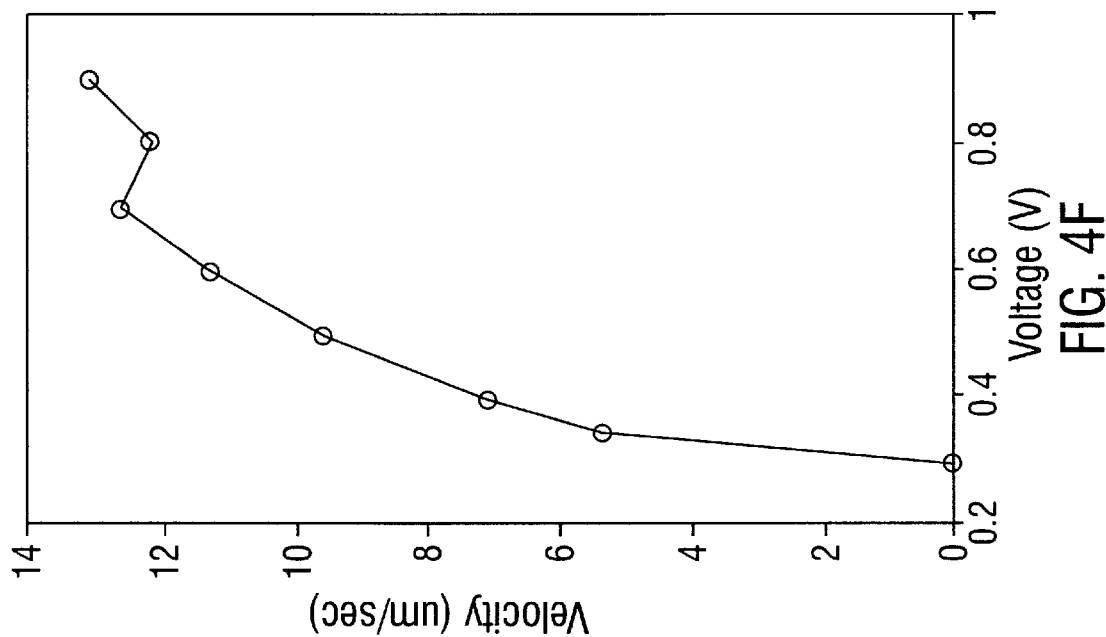
Figure 4E:
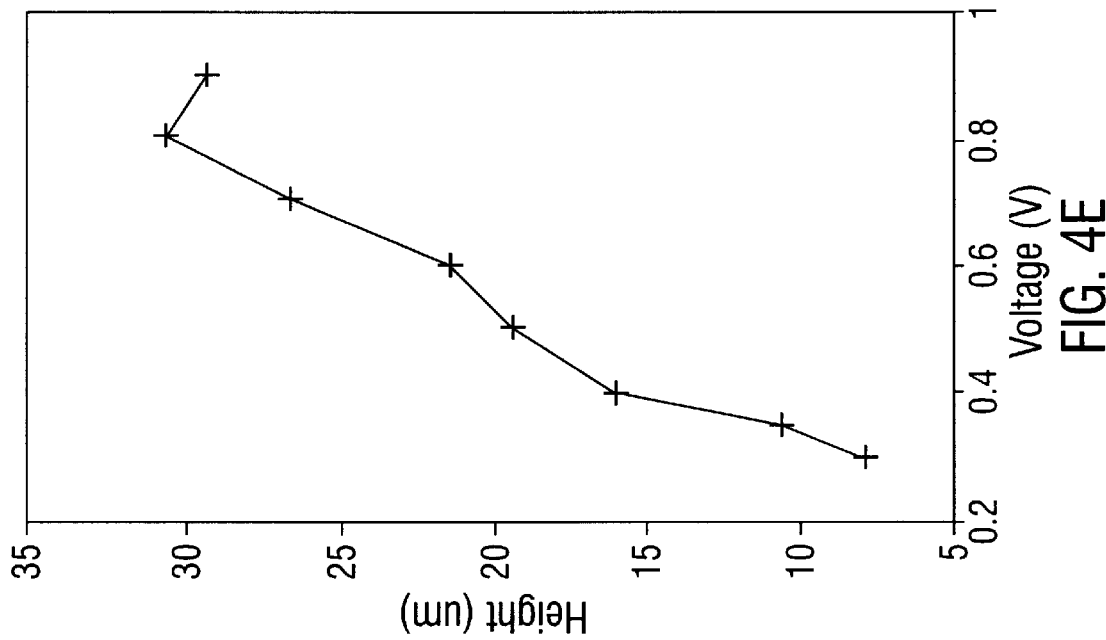

FIG. 2A shows one exemplary embodiment of an apparatus according to the present invention. In this figure, the electrode array 5 is placed on the bottom of a chamber 10; however it is contemplated that the electrode array may be placed on the top and/or bottom walls and/or perimeter walls of a chamber constructed in accordance with the present invention. As shown in FIG. 2B, the spiral electrode array 5 may be comprised of 4 individual electrode elements, EL1–EL4. In this embodiment, the top and bottom walls may be aligned to create a thin chamber. The walls are spaced apart by a spacer 20, which may be, for example, constructed of the same material as the chamber walls, or a TEFLON spacer, a sealing compound, or any other dielectric or conductive material. In an exemplary embodiment, the spacer may be between 200 $\mu$m–300 $\mu$m thick, and more preferably 250 $\mu$m thick. Electrical signals applied to the electrode array 5 create an inhomogeneous alternating electric field that varies with the frequency and magnitude of the input signal. The electrode elements may be provided electrical signals by electrode buses connected to an electrical signal generator. The strength of the electric field is dependent on the applied voltage, position within the chamber, and the size and spacing of electrode elements. For manipulation of mammalian cells, the field strength may be on the order of approximately $1\times10^6$V/m, although this may be much higher for matter placed in an oil medium. The particulate matter desired to be discriminated is introduced into the chamber in a carrier medium that flows into at least one inlet port 15. The inlet port 15 may be, for example, fitted with a plastic tube to allow for introduction and withdrawal of cell suspensions. There may be more than one inlet port however, which permits input of the carrier medium. The carrier medium may be input by a digital syringe pump, a manual syringe, a peristaltic pump, a gravity feed catheter, or the like. As discussed above, the particulate matter may include, for example, biological molecules and non-biological molecules. Also, the matter may include solubilized matter. The carrier medium may be, for example, an eluate consisting of a cell-free suspension buffer, including a mixture of sucrose and dextrose, tissue culture medium, non-ionic or zwitter ionic solutes, or other suspension mediums or non-biological oils, solvents such as phenol alcohol, $CCl_4$, ethylene glycol, or others known in the art. Alternately, one or more ducts may be provided to input a fluid which may be flowed through chamber 10.

The carrier medium may be caused to flow through the chamber at a flow rate which may be on the order of about 0.1 ml/min. to about 100 ml/min., and more preferably about 1 ml/min. to about 100 ml/min. The electric field applied to the electrode elements 5 creates conventional dielectrophoretic forces on the particles in accordance with their dielectric and conductive properties as well as those of the carrier medium.

By controlling the frequency and/or intensity of the applied electric field, the component of the dielectrophoretic force is controlled so as to cause the particles to equilibrate at characteristic distances from the electrode array 5 creating the electric field. In particular embodiments, the dielectrophoretic force may act solely in a vertical direction so as to cause the particles to equilibrate at levitation heights above the chamber bottom wall. This dielectrophoretic force operates in conjunction with the action of the combined hydrodynamic and gravitational forces. Since the dielectrophoretic force acting on each individual particle depends upon its dielectric permittivity and electrical conductivity at the applied frequency, as well as upon its volume, particles having different properties will be positioned at different distances from the electrode element creating the electric field.

The chamber 10 of FIG. 2A may also utilize twDEP forces in addition to cDEP forces, thereby displacing matter in two-dimensions (vertical and horizontal). As discussed above, the cDEP force on the matter causes it to be displaced to a position with respect to the electrode plane. In addition, when the individual electrode elements of spiral array 5 are energized with different phases, a twDEP force on matter which acts substantially parallel to the plane of the electrode elements of spiral array 5 occurs. Therefore, matter is deflected radially across the chamber 10 in a direction towards the center of the spiral array or towards the periphery of the spiral array. Thus, the combined influence of the cDEP and twDEP forces in this embodiment results in a vertical and a horizontal displacement of matter.

In addition to DEP forces, matter in the chamber may be affected by a so-called electrohydrodynamic force. If the carrier medium is a static fluid, the electric field creates an electrodynamic force, which causes a thermal and electrically induced motion of the carrier medium.

Separation in continuous or batch mode is possible. Different embodiments of an apparatus according to the present invention may have additional components connected to the outlet ports 30. For example, particles emerging from the exit ports 30 of the apparatus of the present invention may be collected by one or more fraction collectors, or the like. Additionally, the matter may be measured by one or more measuring or characterizing structures, such as a cytometer, for example. Furthermore, when necessary, particles may be transferred to collection wells containing appropriate solutions or media, such as neutral salt buffers, tissue culture media, sucrose solutions, lysing buffers, solvents, fixatives and the like to trap cells exiting the chamber. In particular embodiments, it may be desired to incorporate sensors within the chamber.

In an apparatus according to the present invention, it is possible to vary the carrier medium characteristics at different heights with respect not only to flow rate but also to fluid density, dielectric permittivity, pH and conductivity. In this way additional particle characteristics may be exploited for particular separation applications.

Methods of Operation

The following descriptions detail construction of an apparatus and methods of operation according to the present invention.

It is understood that the circumstance, width, thickness, number of windings and spacing of electrode arrays may be altered to create electric fields of differing intensities and different inhomogeneity. It is also to be understood that an array of electrodes may be used with the present invention. Further, it is to be understood that the electrode elements need not be parallel, and other geometric configurations, or combinations of configurations, such as serially arranged spiral electrodes, a series of parallel spiral electrodes, three-dimensional spirals and the like may be utilized.

The spiral array may consist of, for example, four parallel elements which may each be connected to a separate channel of an electrical signal generator. The signal generator may be a home-made generator capable of supplying electrical signal to the four individual elements. Other suitable signal generators may include, for example, oscillators, pulse generators, digital output cards, klystrons, RF sources, masers, or the like. The electrode array may be fabricated using standard microlithography techniques, as are known in the art. For example, the electrode array may be fabricated by ion beam lithography, ion beam etching, laser ablation, printing, or electrodeposition. The electrode array of the exemplary embodiment described herein consists of 250 nm gold over a seed layer of 100 nm chromium. In exemplary embodiments, the electrodes may be separated by equal gaps, which may be approximately 20 $\mu$m. This separation is suitable to accommodate the size of breast cancer cells (approximately 12 $\mu$m diameter) so that they are subjected to a continuously traveling electric field. However, other separations may be appropriate for manipulation of different particles. It is understood that the present invention contemplates using electrical signals in the range of about 0 to about 15 V and about 0.1 kHz to about 180 MHz, and more preferably between about 10 kHz and about 10 MHz. In studies which are described below, the signals were provided by a home-made 4-phase signal generator. The signals may be connected from the generator to the electrodes by 50 R coaxial cables. The present invention may utilize a fluid flow of about 0.1 ml/min. to about 500 ml/min., and more preferably between about 1 ml/min and about 50 ml/min. In studies described below, fluid flow in the range of about 1–100 ml/min, was provided by a digital syringe pump.

The following studies were performed:

(1) Investigation of electrokinetic behaviors of MDA-MB-231 human breast cancer cells as a function of the frequency of the applied electrical field Cultured MDA-MB-231 cells (kindly supplied by Dr. Janet Price of M.D. Anderson Cancer Center) were suspended in 8.5% sucrose +0.3% dextrose solutions having, in different measurements, conductivities of 28, 56, 1020, and 2060 mS/m, respectively. Cells exhibited three characteristic effects in sequential order as the frequency of the applied phase-quadrature signals was increased: levitation in the vertical direction and radial motion towards or away from the center of the spiral electrode; transitional behavior, in which cell motion changed from radial motion towards entrapment at electrode edges; and entrapment of cells at the edges of the electrode elements.

At the suspension conductivity of 28 mS/m, cell radial motion occurred in the frequency range of approximately 5 to 32 kHz. With increasing suspension conductivity, the frequency region over which the cell radial motion occurred was progressively widened to between approximately 30 kHz and approximately 10 MHz at a conductivity of 406 mS/m. The transitional behavior of cells occurred in a narrow frequency span that was of a generally constant width on a logarithmic scale but which shifted to higher frequencies as the suspension conductivity was increased. By switching the voltage signals from phase-quadrature to phase-opposition, the regimes of cell radial motion and cell entrapment coincided, respectively, with the frequency ranges where negative and positive cDEP was operative. It is to be understood that phase quadrature means that each element receives one of the signals 0°, 90°, 180° and 270°, in that order. It is further understood that phase opposition means that adjoining elements receive signals 180° phase-shifted from each other. For example, elements EL1 and EL3 may receive signals of 0°, and elements EL2 and EL4 may receive signals of 180°. Phase sequences may be reversed by, for example, a 2-way, 2-pole switch.

Next, the behavior of cells at the suspension conductivity of 56 mS/m for signals of phase 0°, 90°, 180° and 270° connected to the electrode elements EL1 to EL4 of FIG. 2B in sequence was studied. The following modes of cell kinetic responses were observed in different frequency ranges.

Voltage signals in the frequency range of approximately 1 kHz to approximately 10 kHz directed cells to the interelectrode regions and levitated them above the electrode plane to characteristic equilibrium positions in approximately several seconds. In these equilibrium positions, the cells exhibited very little radial motion. The levitation process may be studied, for example, by observing the gradual loss of focus of cells levitating above the focused electrode plane under high-power microscopy. For a fixed frequency, the levitation height generally increased with increasing applied voltage.

When the electrode arrays were energized with voltage signals in the frequency range of approximately 10 kHz to approximately 100 kHz, cells were not only levitated in the vertical direction, but also directed radially towards the center of the electrode geometry. The average velocity for individual cells remained more or less unchanged throughout their inward-moving journeys. The cells appeared to be levitated higher while passing directly over electrode elements. The overall inward motions of cells was independent of the radial angle and was uniform across the whole area covered by the spiral electrode array. Furthermore, each cell exhibited rotation about an axis through its center that was oriented parallel to the electrode surfaces and normal to the radial direction. Reversing the phase sequence of the voltage signals resulted in cell radial motion towards the periphery of the spiral electrode array, and a change in the sense of cell rotation. Close observation showed that individual, isolated cells may differ greatly in their kinetic behaviors, including their radial motion velocity, rotation rate and levitation height, for example. Specifically, some large cells moved radially at velocities up to three times those of smaller ones. When several cells were close to one another, they tended to group together normal to their radial motion and moved faster than single cells. Other cells exhibited a group rolling motion, i.e. all the individual cells exhibited motions along a similar circular path in the plane normal to the angular directions.

In the frequency range of approximately 100 kHz to approximately 300 kHz a transition from radial motion to entrapment occurred. Cell radial motions towards both the spiral center and the periphery occurred. Other cells were loosely trapped at the outward-facing electrode edges, exhibiting fast rotation. Reversing the phase sequence resulted in reversal of cell motion and rotation directions and a change in the trapping positions from the outward to the inward facing edges. As frequency increased from approximately 100 kHz to approximately 300 kHz, the percentage of cells trapped increased from about 20% to about 90%, while fewer trapped cells showed a preference towards one electrode edge.

Upon application of voltage signals between approximately 300 kHz and approximately 100 MHz, cells were quickly directed towards the nearest electrode edge and were trapped there, independently of their initial positions. Cells exhibited little or no rotational effects. Reversing the phase sequence did not affect cell entrapment, except at frequencies between approximately 30 MHz and approximately 60 Mhz, where about 50% of the cells showed a trapping-edge preference depending on the phase-sequences applied. In this case, these cells were trapped at the inward facing electrode edges when phases 0°, 90°, 180° and 270° were connected to the electrode elements in sequence from the spiral center.

The velocity of cell radial motion was found to depend on the suspension conductivity and the frequency and magnitude of the applied voltage signals. The frequency dependency of the mean velocity of (typically 10) individual cells was determined at different suspension conductivities as the cells traveled at least 40 $\mu$m by an applied voltage of approximately 0.75 V RMS. At each conductivity, the mean cell velocity increased with increasing frequency up to the transition range where some cells changed directions of their radial motions. Increasing the frequency further resulted in entrapment of all cells at the electrode element edges. The large standard deviations of cell velocities at each conductivity studied confirmed that inhomogeneities existed in cell kinetic behavior. Individual cell velocities were as high as 30 $\mu$m/sec.

Radial cell velocity is also dependent on the applied voltage. For a suspension conductivity of 56 mS/m and a field frequency of approximately 50 kHz, a voltage threshold of approximately 0.2 V exists under which cell radial motion did not occur. Above approximately 0.2 V, cell velocity increased steadily with applied voltage until a plateau was reached. As the applied voltage was increased above approximately 0.85 V, cell velocity gradually decreased.

Cell levitational effects were also found to be closely dependent on suspension conductivity and the frequency and magnitude of the applied voltages. At approximately 50 kHz and a suspension conductivity of 56 mS/m, there existed a voltage threshold of approximately 0.2 V, below which the cell levitation was not possible. Above approximately 0.2 V, the cell positions steadily increased with applied voltage up to approximately 1 V, where the levitation height became almost independent of further voltage increase.

An analysis of these kinetic effects using generalized dielectrophoresis theory in conjunction with the electric field distribution allows the dielectric characteristics of MDA-MB-231 cells to be derived. Conversely, such knowledge of the dielectric properties of matter in advance makes it possible to predict the conditions for achieving desired matter manipulations using the phenomena described above. Further, an unknown sample of matter may be introduced into the chamber and be subjected to the same electric field distribution applied to the known matter. In this way, an unknown sample may be diagnostically tested to determine the presence of the known matter.

Further results from tests are shown in FIGS. 3A–3F and FIGS. 4A–4F. FIGS. 3A–3F show the frequency dependencies of levitation height and radial motion velocity of individual cells in a spiral electrode array having a voltage of 0.78 Vrms. FIGS. 4A–4F show the voltage dependencies of levitation height and radial motion velocity of individual cells in a spiral electrode array.

FIG. 3 shows the frequency dependencies of levitation height and radial motion velocity of individual cells in a spiral electrode array having a voltage of 0.7 V (RMS).

(A & B) cell radius=5.94 $\mu$m, suspension conductivity= 180 $\mu$S/cm;

(C & D) cell radius=6.93 $\mu$m, suspension conductivity= 560 $\mu$S/cm;

(E & F) cell radius=7.11 $\mu$m, suspension conductivity= 1600 $\mu$S/cm;

FIG. 4 shows the voltage dependencies of levitation height and radial motion velocity of individual cells in a spiral electrode array.

(A & B) cell radius=5.94 $\mu$m, suspension conductivity= 180 $\mu$S/cm, 25 kHz;

(C & D) cell radius=7.38 $\mu$m, suspension conductivity= 560 $\mu$S/cm, 80 kHz;

(E & F) cell radius=6.12 $\mu$m, suspension conductivity= 1600 $\mu$S/cm, 275 kHz;

These results demonstrate the sensitive dependency of cell levitation and radial motion velocity on applied field frequency and field voltages. Theoretical analysis of these data, in combination with the calculation of DEP forces acting on cells indicate that the spiral electrodes can readily distinguish cells of very close dielectric characteristics by height and/or radial motion velocity. For example, two cells of identical size with differences in their membrane capacitance as small as 10% can be distinguished and separated with the electrode array of the present invention.

(2) Separation of MDA-MB-231 cells from human blood

In this study, the chamber was preloaded with a mixture of MDA-MB-231 cells and human blood cells in the ratio 1:10 at a total concentration of approximately $1 \times 10^7$ cells/ml supported in an 8.5% sucrose+0.3% dextrose solution having a conductivity of 10 mS/m. The following sequence of voltage signals was applied:

A voltage of approximately 0.7 V RMS at approximately 40 kHz was applied to the electrodes 1–4 with the sequence of phase values 0°, 90°, 180° and 270°. MDA-MB-231 cells were trapped at the edges of the electrode elements while blood cells (mainly erythrocytes) were levitated and directed to the periphery of the spiral electrode array. After approximately 20 seconds of voltage application, all erythrocytes had moved out of the spiral region.

A voltage of approximately 0.7 V RMS at approximately 20 kHz was applied to EL1–EL4 with the sequence of phase value 270°, 180°, 90° and 0°. Under this new field condition, MDA-MB-231 cells were levitated and transported to the center of the spiral. In this way the isolation/separation of dilute MDA-MB-231 cells from human blood cells was demonstrated.

Figure 5A:
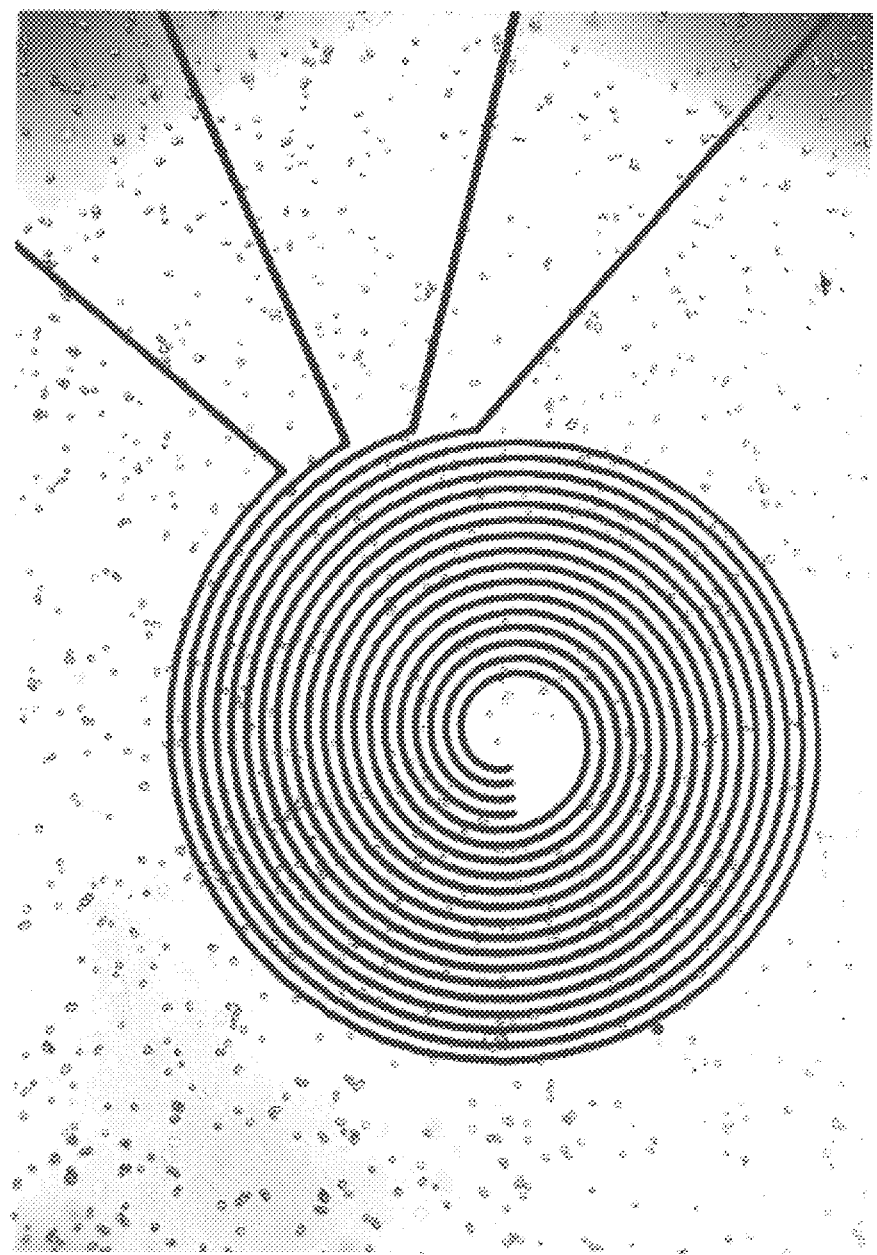
FIGS. 5A and 5B show the radial motion of MDA231 cells towards the electrode array periphery.
Figure 5B:
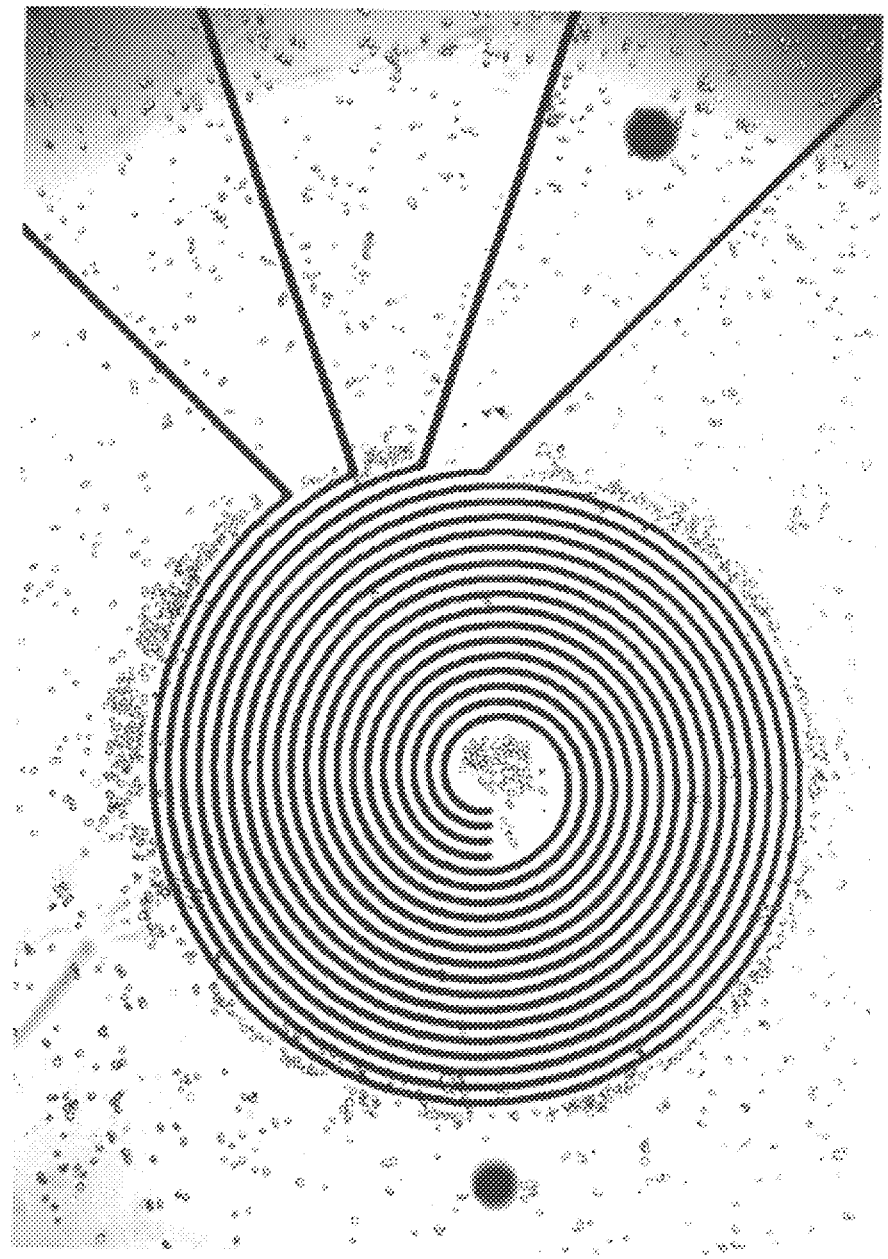

FIGS. 5A and 5B show the radial motion of MDA-231 cells towards the electrode array periphery. Prior to application of AC electrical fields, MDA231 cells are randomly distributed on the spiral electrode array, as shown in FIG. 5A. By changing the phase sequence of the voltage signals to the electrode elements, phase values of the field components at the periphery of the electrode array attain maxima. The phase sequence to attain this configuration is shown in FIG. 2B. For a suspension conductivity of approximately 100 mS/m, MDA231 cells are directed towards the periphery at a frequency of approximately 75 kHz, as shown in FIG. 5B.

Figure 6A:
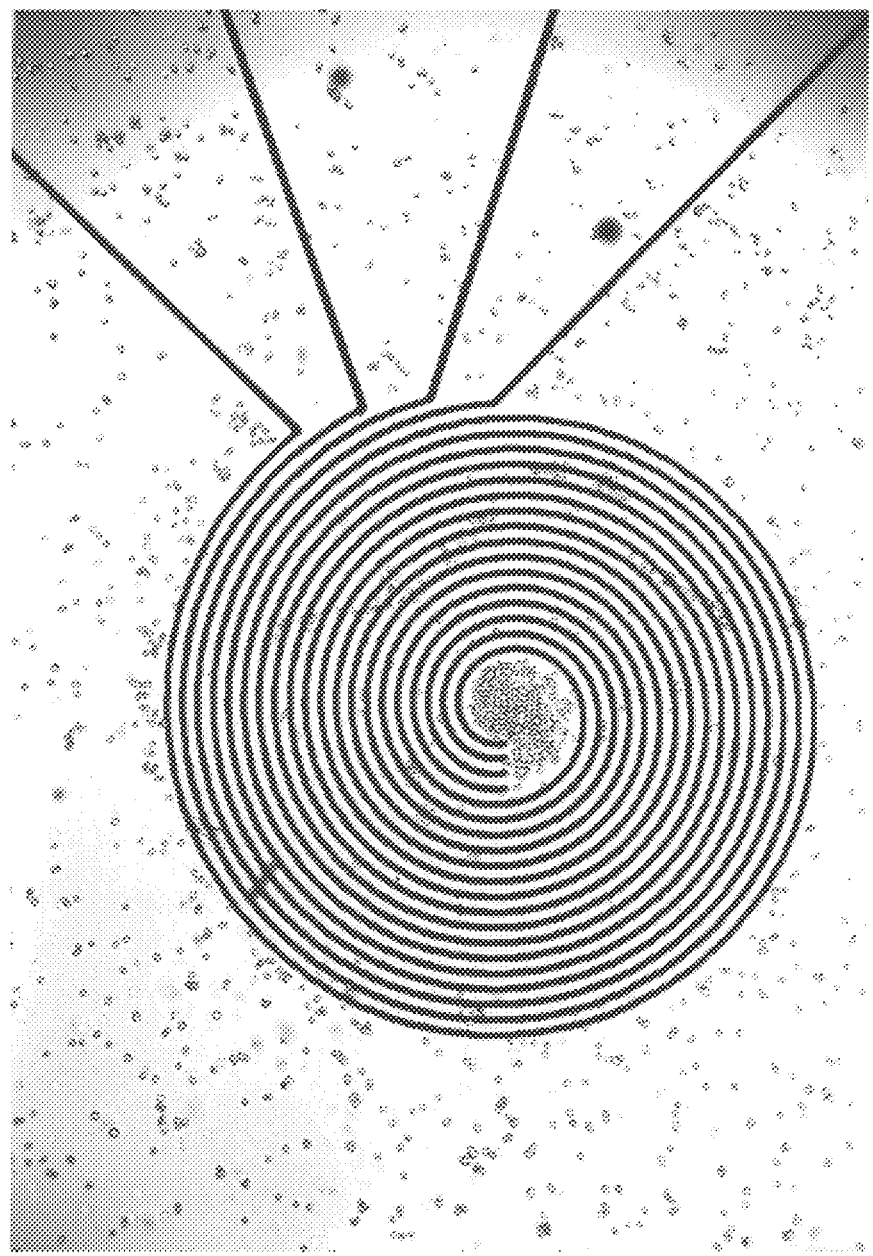
FIGS. 6A and 6B show the radial motion of MDA231 cells towards the electrode array center.
Figure 6B:
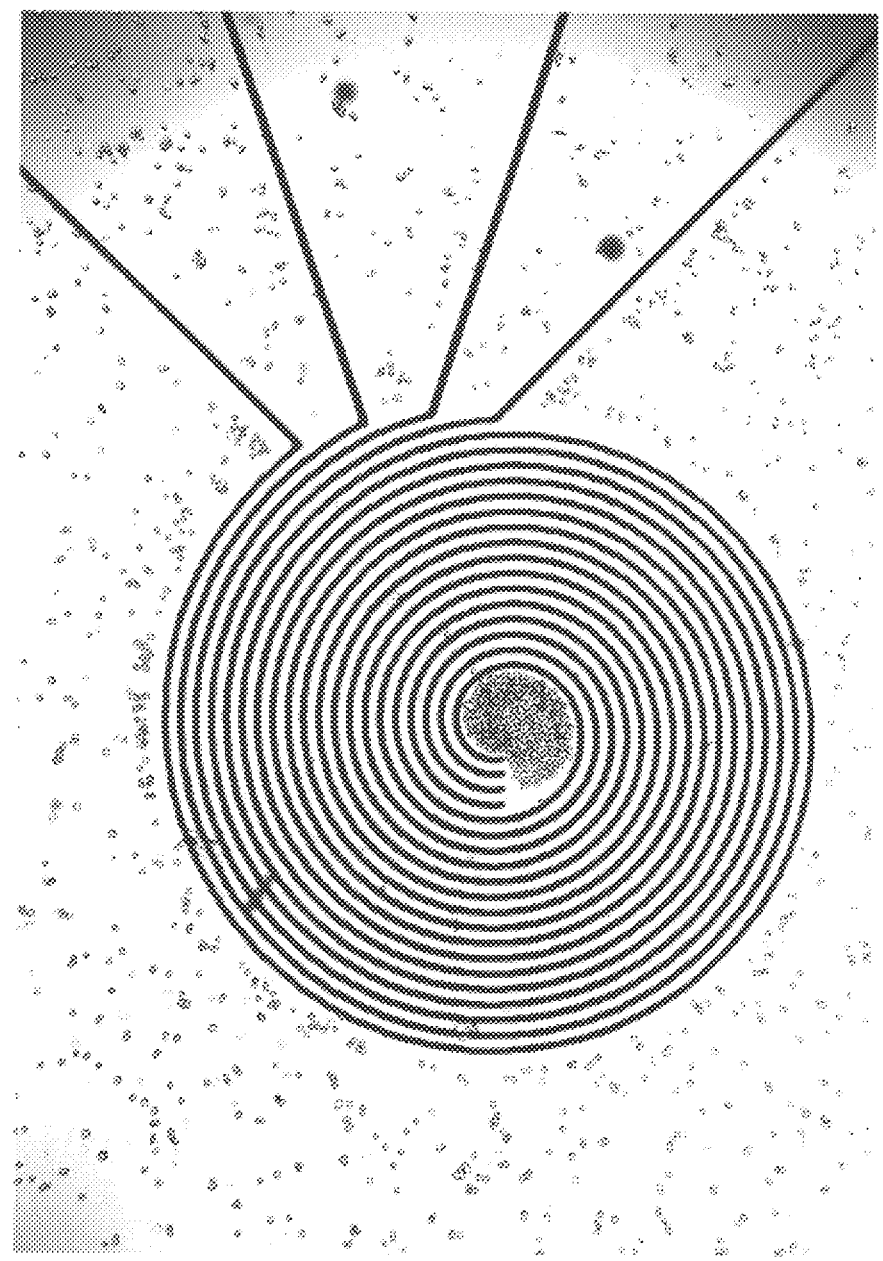

FIGS. 6A AND 6B show radial motion of MDA231 cells towards the center of the electrode array. FIG. 6A shows cell position several seconds after application of a signal to the electrode elements. By changing the phase sequence of the voltage signals to the electrode elements to the opposite of that shown in FIG. 6B, maxima of phase distributions of the field components occur at the center of the electrode array. For a suspension conductivity of approximately 100 mS/m, MDA231 cells are directed towards the electrode center at a frequency of 75 kHZ, as shown in FIG. 6B.

Figure 7A:
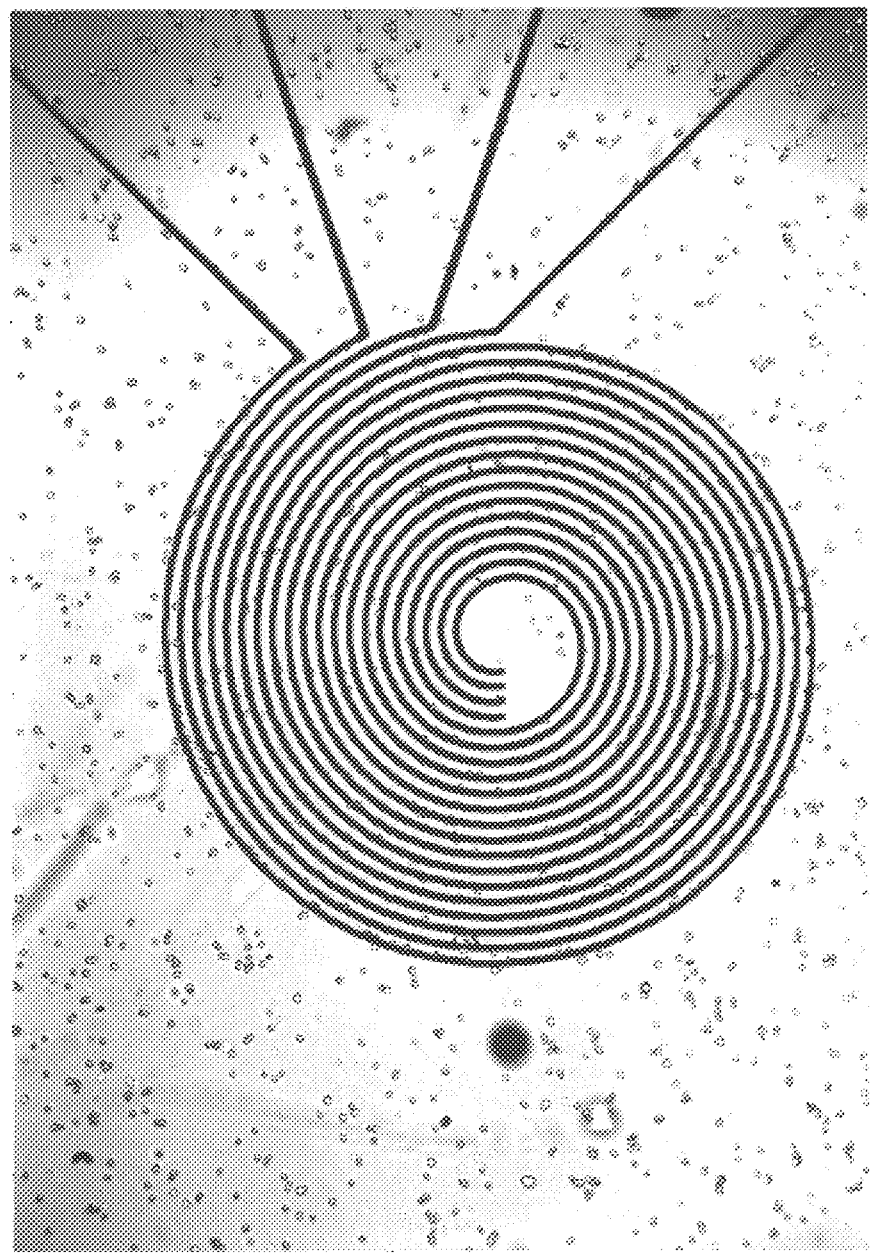
FIGS. 7A and 7B show MDA231 cells trapped at electrode edges.
Figure 7B:
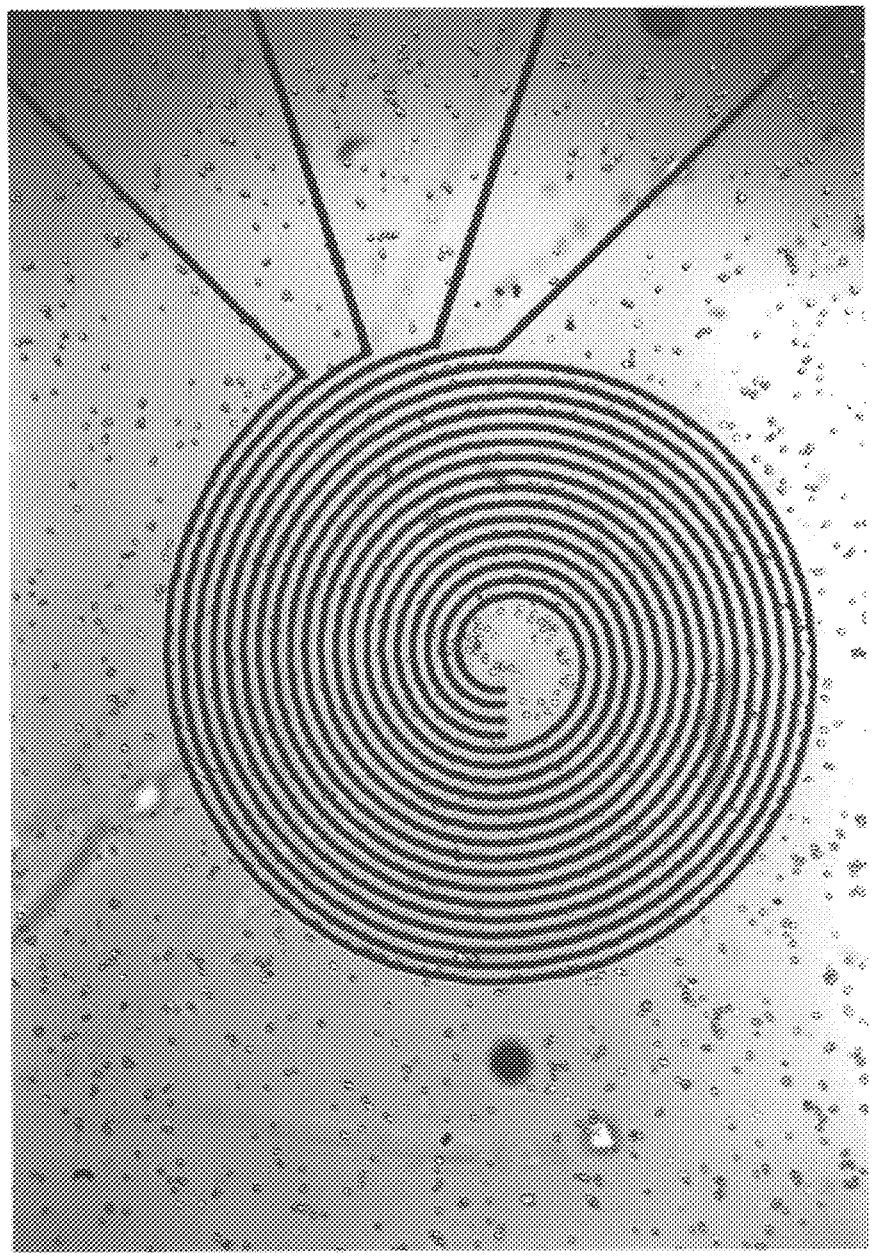

FIGS. 7A and 7B show the entrapment of MDA231 cells at the electrode edges. Application of voltage signals at high frequencies (>approximately 200 kHz) causes entrapment of MDA 231 cells at the electrode edges. For a frequency of approximately 200 kHz, cell entrapment shows a preference to the inward facing (FIG. 7A) or the outward-facing (FIG. 7B) electrode edges. This is caused because of the nonsymmetric distribution of the traveling wave DEP force with respect to the electrode elements.

Figure 8A:
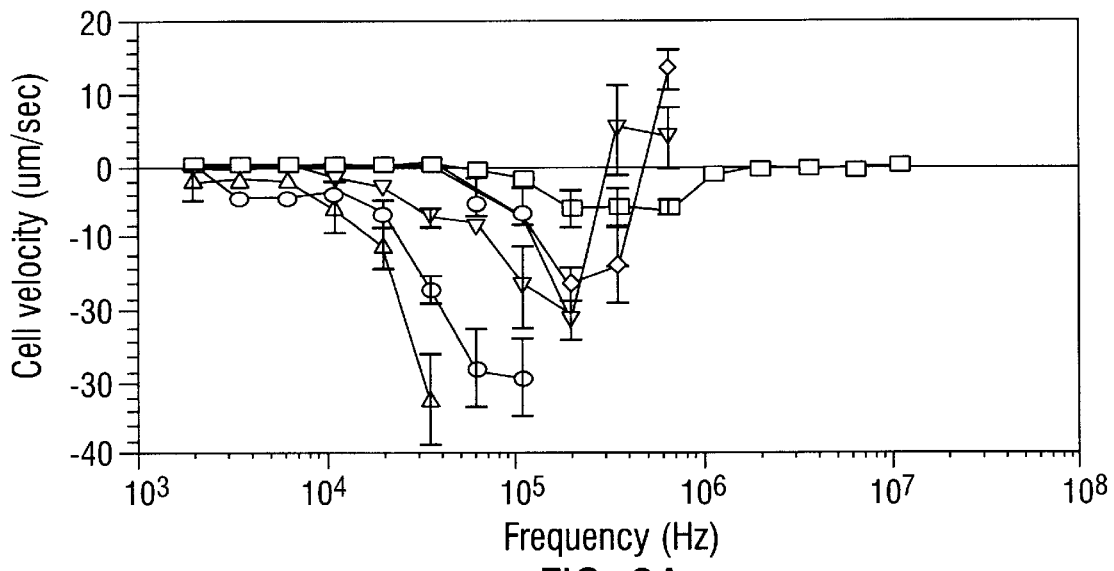
FIG. 8A shows frequency dependence of cell radial velocity.

FIG. 8A shows the frequency dependence of the velocity of cell radial motion at different suspension conductivities. At each conductivity radial motion occurs for only a particular frequency range, in which cell velocity increases with frequency. With increasing suspension conductivity, the frequency region of radial motion shifts towards higher values and cell velocity decreases.

Figure 8B:
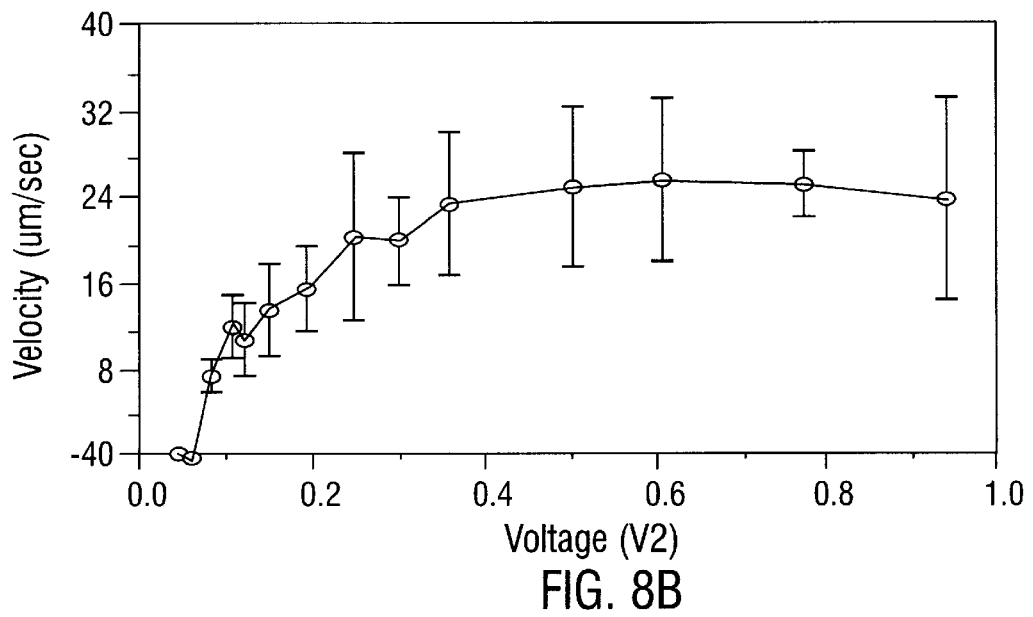
FIG. 8B shows voltage dependence and cell radial velocity.

FIG. 8B shows the voltage dependence of the velocity of cell radial motion (suspension conductivity of approximately 56 mS/m).

Figure 8C:
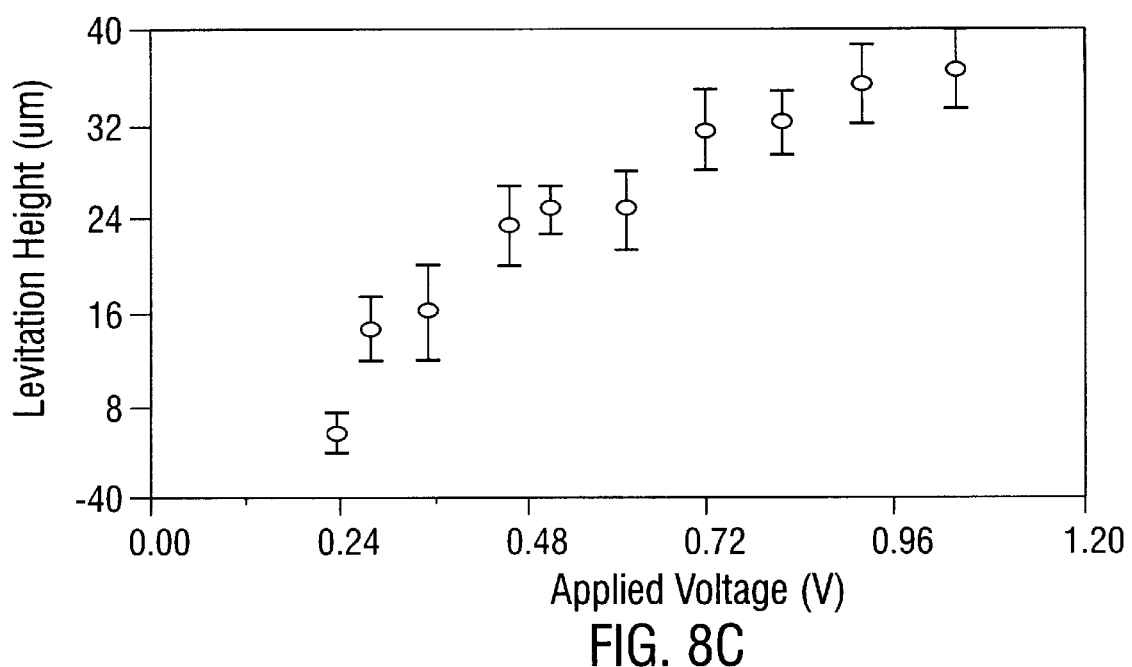
FIG. 8C shows voltage dependence of cell levitation height.
Figure 9A:
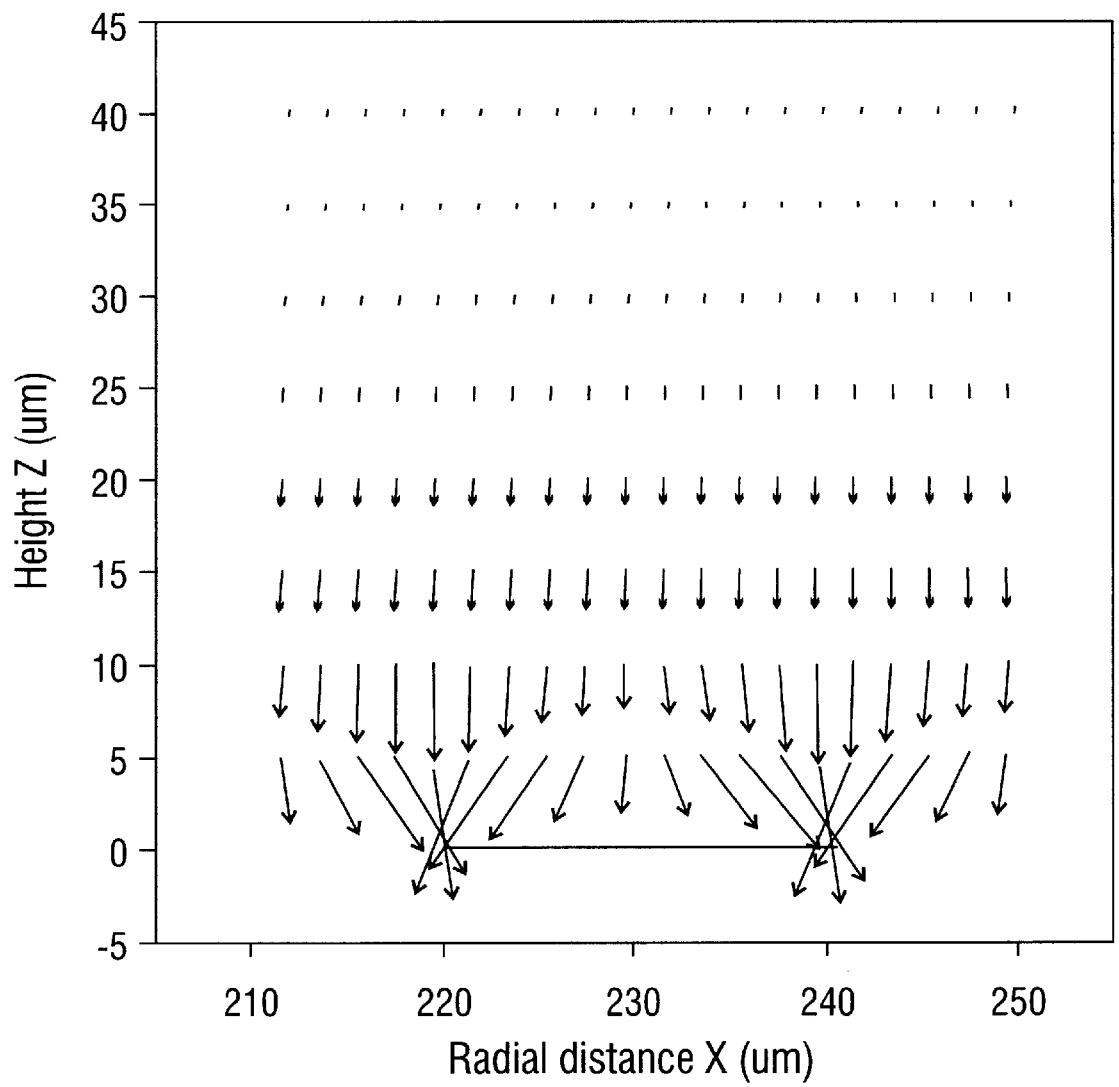
FIG. 9A shows vector distribution of field magnitude non-uniformity factor produced by a spiral electrode array energized by phase-quadrature signals.
Figure 9B:
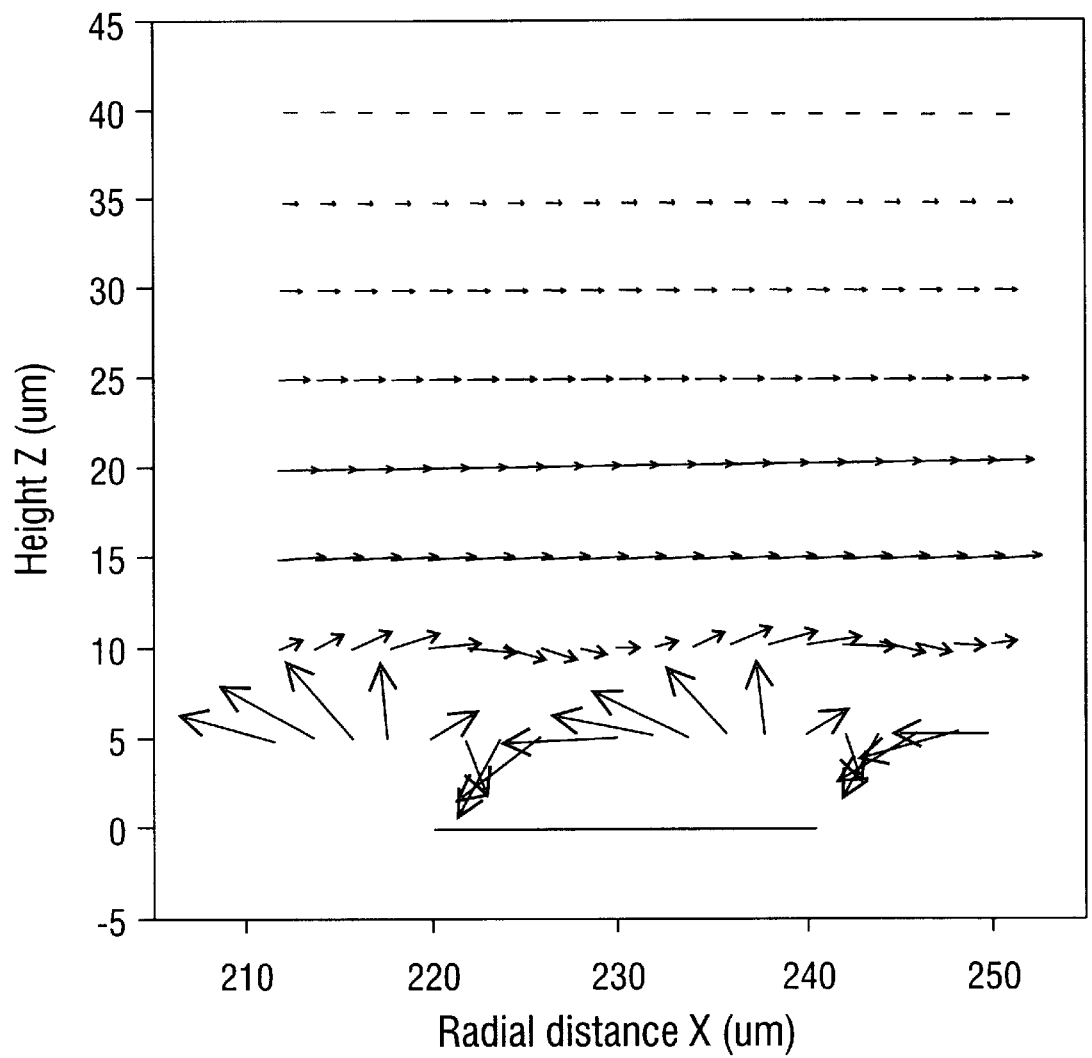
FIG. 9B shows vector distribution of field phase non-uniformity factor produced by a spiral electrode array energized by phase-quadrature signals.
Figure 10:
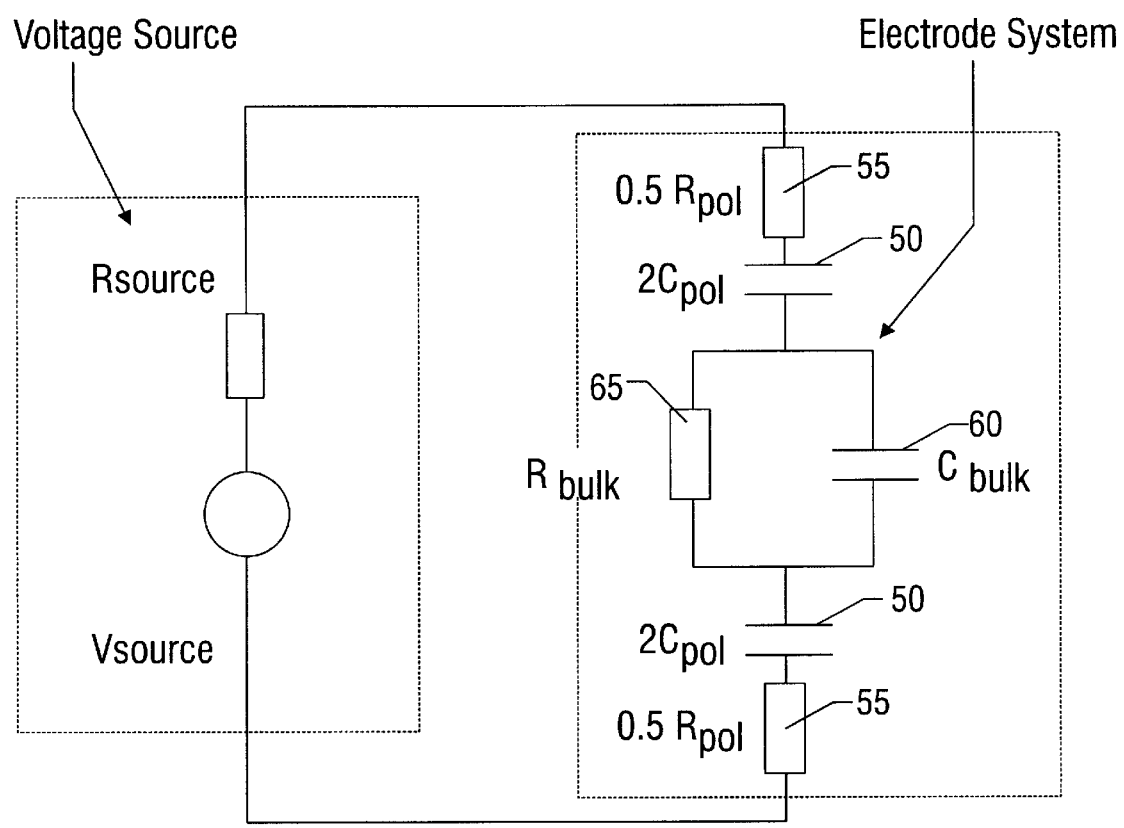
FIG. 10 shows equivalent circuits for the electrode system of the present invention.

FIG. 8C shows the voltage dependence of cell levitation height (suspension conductivity of approximately 56 mS/m and signal frequency at 50 kHz).

It is contemplated that the apparatus and methods according to the present invention may be used for cell or particle characterization, as a diagnostic tool to identify, for example, cancer cells or other cells that are desired or of interest to the clinician, and as a therapeutic tool to purge a patient sample of undesired cells or other particle.

For example, the methods according to the present invention may be used to characterize the physical properties of an unknown particulate matter. A sample including an unknown biological or organic or mineral sample may be input into the chamber and separated according to the procedures set forth above. Following separation and removal of extraneous particles, the unknown particle may be collected at an output port of the chamber. The particle can then be analyzed using standard particle characterization techniques known in the art, such as those used in diagnostic microbiology and in histology, for example, electron microscopy. After determining characteristics that are unique to a particle, an investigator may then compare these characteristics to the known characteristics of a particle. Therefore, the researcher may determine whether the unknown particle is the same as a known particle, or whether it has similar properties.

In addition, the invention contemplates the characterization of known particles, which may then be used as a reference tool for determining unknown particles based on similar trapping frequencies, voltages, flow rates, and other parameters set forth above. The sample may be introduced into the chamber of the present invention and then be subjected to the separation methods detailed above. By performing these separation techniques, the trapping frequency and release frequency of the particle can be determined. These values are then useful in comparing similar parameters of an unknown sample to this known sample. Certain clinical applications requiring separation of a known particle from an unknown particle would require such values to complete the methods of separation.

A clinical application of the present invention would be to use the present apparatus and methods as a diagnostic tool to screen unknown samples for the presence or absence of various cell types. First, as set forth previously, a patient's sample may be placed in the apparatus, and various cell types may be separated based on previously determined parameters or characteristics. These cells may include cancer cells, or cells infected with bacteria, viruses, protozoans, or parasites, bacteria, viruses protozoans, or they may include cells that are deficient in certain enzymes or cell organelles, altered biopsies, plaques and scrape tests including Pap smears and so forth. For example, the present invention may be used to concentrate all bacteria from a urine sample and exploit differences in the dielectric properties of gram positive and gram negative bacteria. Further, the present invention may be used to quickly detect the presence of several cells infested with malaria from a large sample size. Additionally, the present invention may be used to isolate highly dispersed tumor cells from normal cell mixtures such as blood and bone marrow. Thus, it is well within the scope of the invention to separate all types of particles that have differential sedimentation rates in a fluid stream, based on size, density, dielectric strength, and conductivity, for example. Therefore, the present invention may be used to diagnose the presence of a condition, for example, a cancer, or other cellular disorder.

Another clinical application would be to use the apparatus and methods of the present invention to separate unwanted cells, such as cancerous cells, from a cell population including wanted or normal cells. For example, once a cancer has been detected, for instance in bone marrow, a patient's bone marrow may be input into an apparatus according to the present invention to separate the cancer cells, or preneoplastic cells, from normal cells. These normal cells may then be collected at the output of the chamber and returned to the patient, while the unwanted cancer cells may be later collected at the output of the chamber and characterized, utilized in further studies, or discarded. In this manner, unwanted cells are purged from a normal cell population, while at the same time a particular cell type is enriched, such as tumor cells, normal cells, progenitor cells, etc.

The apparatus and methods disclosed and claimed herein can be made and executed without undue experimentation in light of the present disclosure. While the apparatus and methods of this invention have been described in terms of preferred embodiments, it will be apparent to those of skill in the art that variations may be applied to the apparatus, methods and in the steps or in the sequence of steps of the method described herein without departing from the concept, spirit and scope of the invention. All substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Arnold, W. M. el al. (1982) *Naturwisenischaften* 69,297–300.
2. Beckeretal. (1995) *Proc. Natl. Acad. Sci.* 92,860–864.
3. Becker, F. F. et al. (1994) *J Phys. D. Appl. Phys.* 27(12),2659–2662.
4. Boyum, A. (1974) *Tissue Antigens* 4, 269–274.
5. Buck, R. P. (1992)*Ann. Biomed. Eng.*, 20:363–383.
6. Cantrell, D. A. et al. (1992) *Ciba. Found Symp.* 164, 208–222.
7. Chess, L. et al. (1976) in: *In vitro Methods in Cell Mediated and Tumor Immunity,* 255–261.
8. Fischer, A. (1993)*Brit. J Haematol.* 83, 531–534.
9. Fuhr, G. (1985) Über die rotation dieelektrischer körper in rotierenden feldern, Ph.D. Dissertation,, Berlin, Chap. 3, 24–53.
10. Gascoyne,P. R. C. et al. (1994) *IEEE. Trans. Ind. Appl.* 30, 829–834.
11. Gascoyne, P. R. C., et al. (1992) *Meas. Sci. Technol.* 3,439–445.
12. Giddings, J. C., (1993) *Science* 260, 1456–1465.
13. Hagedorn, R. et al. (1992) *Electrophoresis* 13,49–54.
14. Holzel, R. et al. (1992) *Biochim. Biophyus. Acta* 1101, 195–200.
15. Huang,Y. et al. (1992)*Phys. Med. Biol.* 37,1499–1517.
16. Huang,Y.et al. (1993) *Phys. Med. Biol.* 37,1499–1517.
17. Jaron, D. et al. (1968) *Med. Biol. Eng.*, 6:579–594.
18. Markx, G. H. et al. (1994) *Microbiology* 140,585–591.
19. Schwan, H. P. (1992) *Ann. Biomed. Eng.*, 20:269–288.
20. Smeland, E. B. et al (1992) *Leukemia*, 6, 845–852.
21. Smeland et al., (1992) *Leukemia*, 6:845–852.
22. Stout, R. D. (1993) *Curr. Opin. Immunol.* 5(3), 398–403.
23. Wang, X.-B. et al. (1994) *Biochim. Biophys. Acta* 1193,330–344.
24. Wang, X.-B. et al. (1993)*J Phys. D: Appl. Phys.* 26,1278–1285.

What is claimed is:

1. An apparatus for the discrimination of matter utilizing dielectrophoresis comprising:
   a chamber having an interior surface and an exterior surface;
   at least one spiral electrode element positioned along a portion of said chamber; and
   an electrical signal generator to energize said at least one spiral electrode element and create an electric field that causes a dielectrophoretic force on said matter within said chamber, thereby displacing said matter to positions within said chamber.

2. The apparatus according to claim 1, further comprising one inlet port and one outlet port within said chamber.

3. The apparatus according to claim 1, further comprising a plurality of spiral electrode elements arranged in a spiral electrode array.

4. The apparatus according to claim 3, wherein each of said plurality of spiral electrode elements is individually connected to one of a plurality of electrical conductors electrically connected to an electrical signal generator.

5. The apparatus according to claim 3, wherein each of said plurality of spiral electrode elements is energized at different phases to create an energized spiral electrode array.

6. The apparatus according to claim 5, wherein said energized spiral electrode array further creates a traveling electric field.

7. The apparatus according to claim 3, wherein the spiral electrode array is configured on a top wall of said chamber.

8. The apparatus according to claim 3, wherein the spiral electrode array is configured on a bottom wall of said chamber.

9. The apparatus according to claim 3, wherein a plurality of said spiral electrode arrays are adapted on opposing surfaces of said chamber.

10. The apparatus according to claim 1, wherein said dielectrophoresis comprises conventional dielectrophoresis.

11. The apparatus according to claim 1, wherein said dielectrophoresis comprises traveling wave dielectrophoresis.

12. The apparatus according to claim 1, wherein said dielectrophoresis comprises generalized dielectrophoresis.

13. The apparatus according to claim 1, wherein the chamber includes a top wall, a bottom wall, and a peripheral wall.

14. The apparatus according to claim 1, wherein said matter comprises particulate matter.

15. The apparatus according to claim 14, wherein the particulate matter comprises a cell, cell aggregate, cell organelle, nucleic acid, bacteria, protozoan, or virus.

16. The apparatus according to claim 1, wherein said matter comprises solubilized matter.

17. The apparatus according to claim 16, wherein the solubilized matter comprises a molecule, molecular aggregate, or molecule mixture.

18. The apparatus according to claim 17, wherein the molecule or molecular aggregate comprises a protein or a protein mixture.

19. The apparatus according to claim 1, wherein the at least one spiral electrode element is positioned along the interior surface of said chamber.

20. The apparatus according to claim 1, wherein the at least one spiral electrode element is adapted along the exterior surface of said chamber.

21. The apparatus according to claim 1, wherein said at least one electrical signal is provided by an electrical signal generator.

22. The apparatus according to claim 1, in which said at least one electrical signal comprises at least three electrical signals provided at different phases.

23. A method of discriminating matter utilizing dielectrophoresis, comprising:

providing a chamber, said chamber having an interior surface and an exterior surface and at least one spiral electrode element positioned along a portion of said chamber;

introducing said matter into said chamber;

applying at least one electrical signal to said at least one spiral electrode element to create an energized at least one spiral electrode element to cause a dielectrophoretic force on said matter; and wherein said matter is displaced to positions within said chamber, thereby discriminating said matter according to its positions within said chamber.

24. The method according to claim 23, wherein said at least one electrical signal is provided by an electrical signal generator.

25. The method according to claim 23, wherein said energized at least one spiral electrode element creates a spatially inhomogeneous electric field.

26. A method according to claim 25, wherein said spatially inhomogeneous electric field causes said matter to be attracted to said at least one spiral electrode element.

27. A method according to claim 26, further comprising holding said matter in close proximity to said at least one spiral electrode element.

28. A method according to claim 26, wherein said spatially inhomogeneous electric field causes said matter to be repelled from said at least one spiral electrode element.

29. The method according to claim 23, further comprising at least three electrical signals provided at different phases to create a traveling electric field.

30. The method according to claim 23, wherein the matter is particulate matter.

31. The method according to claim 30, wherein the particulate matter comprises a cell, cell aggregate, cell organelle, nucleic acid, bacteria, protozoan, or virus.

32. The method according to claim 30, wherein the particulate matter comprises a mixture of cell types.

33. The method according to claim 32, wherein the mixture of cell types include cancer cells to be discriminated.

34. The method according to claim 32, wherein the mixture of cell types are a mixture of blood cells and breast cancer cells, said breast cancer cells to be discriminated.

35. The method according to claim 23, wherein said matter is solubilized matter.

36. The method according to claim 35, wherein the solubilized matter comprises a molecule, or molecular aggregate.

37. The method according to claim 36, wherein the molecule or molecular aggregate is a protein.

38. The method according to claim 23, further comprising varying said at least one electrical signal, thereby causing changes in displacement of said matter, thereby further discriminating said matter according to its positions within said chamber.

39. A method according to claim 23, wherein said matter includes desired matter and nondesired matter.

40. A method according to claim 39, in which said nondesired matter is held in close proximity to said at least one spiral electrode element and said desired matter is partitioned by said dielectrophoretic force.

41. A method according to claim 40, further comprising changing said at least one electrical signal, thereby releasing said nondesired matter from close proximity to said at least one spiral electrode element and partitioning said nondesired matter by said dielectrophoretic force.

42. A method according to claim 39, in which said desired matter is held in close proximity to said at least one spiral electrode element and said nondesired matter is partitioned by said dielectrophoretic force.

43. A method according to claim 42, further comprising changing said at least one electrical signal, thereby releasing said desired matter from close proximity to said at least one said plurality of electrode element and partitioning said desired matter by said dielectrophoretic force.

44. A method of determining characteristics of an unknown matter utilizing dielectrophoresis, comprising:

providing a chamber having an interior surface and an exterior surface; a spiral electrode array positioned along a portion of said chamber;

introducing a mixture including said unknown matter into said chamber;

applying at least one electrical signal having an initial frequency to said spiral electrode array at different phases to create an energized spiral electrode array to cause a dielectrophoretic force on said unknown matter; and varying said initial frequency until said unknown matter is caused to be moved to a central portion of said spiral electrode array at a discriminating frequency.

45. The method of claim 44, further comprising collecting said unknown matter at an outlet port of said chamber.

46. The method of claim 44, further comprising characterizing said unknown matter to identify said unknown matter.

47. A method for diagnosing a condition by determining a presence of unidentified matter in a patient sample utilizing dielectrophoresis, comprising:

obtaining a chamber having an interior surface and an exterior surface; a spiral electrode array positioned along a portion of said chamber;

introducing a mixture including said unidentified matter into said chamber;

applying at least one electrical signal to said spiral electrode array at different phases at a discriminating frequency of a known matter to create a traveling electric field to cause a dielectrophoretic force on said mixture; and determining whether said unidentified matter is moved to a central portion of said spiral electrode array, indicating said condition.

48. An apparatus for the discrimination of matter, comprising:

a chamber having an interior surface and an exterior surface, a top wall, a bottom wall and a peripheral wall;

a spiral electrode array positioned along a portion of at least one of said walls;

an electrical signal generator electrically connected to said spiral electrode array; and wherein said spiral electrode array energized at different phases by at least one electrical signal provided by said electrical signal generator creates an electric field in said chamber, thereby causing at least one dielectrophoretic force on said matter.

* * * * *